United States Patent [19]

Thompson et al.

[11] Patent Number: 5,277,913
[45] Date of Patent: Jan. 11, 1994

[54] LIPOSOMAL DELIVERY SYSTEM WITH PHOTOACTIVATABLE TRIGGERED RELEASE

[76] Inventors: David H. Thompson, 12602 NW. Barnes Rd. Apt. 6, Portland, Oreg. 97229; Valerie C. Anderson, 1862 Woodland Ter., Lake Oswego, Oreg. 97034

[21] Appl. No.: 756,504

[22] Filed: Sep. 9, 1991

[51] Int. Cl.$^5$ .......................................... A61K 9/127
[52] U.S. Cl. ................................... 424/450; 424/417; 428/402.2; 436/829
[58] Field of Search ............... 424/450, 417; 436/829; 428/402.2

[56] References Cited

U.S. PATENT DOCUMENTS 4,882,165 11/1989 Hunt et al. ........................ 424/450

FOREIGN PATENT DOCUMENTS 2209458A 5/1989 United Kingdom .
2209468 5/1989 United Kingdom .

OTHER PUBLICATIONS

Morand, JBC, 23, 11597 (1988).
Kusumi et al. Chemistry Letters 433 (1989).
Boggs et al., "Influence of Ether Linkage of the Lamellar to Hexagonal Phase of Transition of Ethanolamine Phospholipids," Biochemistry 20:5728-5735 (1981).
Brault, et al. "Fundamental aspects in tumor photochemotherapy: interactions of porphyrins with membrane model systems and cells," Biochimie 68:913-921 (1986).
Fielding, "The Use of Inhaled Liposome Formulations for Drug Delivery to the Lungs and Systemic Circulation," Proc. West. Pharmacol. Soc. 32:103-106 (1989).
Frankel et al., "Photoinduced Destabilization of Bilayer Vesicles," J. Am. Chem. Soc. 111:9262-9263 (1989).
Kano et al., "Photoresponsive Artificial Membrane. Regulation of Membrane Permeability of Liposomal Membrane by Photoreversible Cis-Trans Isomerization of Azobenzenes," Photochemistry and Photobiology 34:323-329 (1981).
Kusumi et al., "Liposomes That Can Be Disintegrated by Photo-Irradiation," Chemistry Letters 433-436 (1989).
Morand et al., "Disappearance of Plasmalogens from Membranes of Animal Cells Subjected to Photosensitized Oxidation," J. of Biological Chem. 23:11597-11606 (1988).

(List continued on next page.)

Primary Examiner—Thurman K. Page
Assistant Examiner—G. S. Kishore
Attorney, Agent, or Firm—Klarquist, Sparkman, Campbell, Leigh & Whinston

[57] ABSTRACT

A triggered release liposomal delivery system is disclosed that selectively releases its contents in response to illumination or reduction in pH. The liposomes contain an amphipathic lipid, such as a phospholipid, having two chains derived from fatty acid that allow the lipid to pack into a bilayer structure. One or both of the alkyl chains contains a vinyl ether functionality that is cleaved by reactive oxygen species (ROS) or acid. A photosensitizer is incorporated into the liposomal cavity or membrane, and produces ROS or acid when illuminated to cleave the vinyl ether functionality and disrupt the liposomal membrane to release the vesicle contents. The lipid is preferably a plasmalogen, for example $$CH_2-O-CH=CHR_1$$
$$CH-O-C-R_2$$
$$CH_2O_2P(O)O-R_3$$

wherein $R_1$ and $R_2$ are each long chain hydrocarbons containing 12-24 carbons.

27 Claims, 9 Drawing Sheets

OTHER PUBLICATIONS

O'Brien et al. "Light-regulated permeability of rhodopsin: egg phosphatidylcholine recombinant membranes," Proc. Natl. Acad. Sci. USA 74:5222–5226 (Dec. 1977).

O'Brien, "Light-Regulated Permeability of Rhodopsin-Phospholipid Membrane Vesicles," Photochemistry and Photobiology 29:679–685 (1979).

Ostro et al., "Use of liposomes as injectable-drug delivery systems," Am. J. of Hospital Pharmacy 46:1576–1587 (1989).

Perez-Soler, "Liposomes as carriers of antitumor agents: toward a clinical reality," Cancer Treatment Reviews 16:67–82 (1989).

Pidgeon et al., "Light Sensitive Liposomes," Photochemistry and Photobiology 37:491–494 (1983).

Ranade, "Drug Delivery Systems. 1. Site-Specific Drug Delivery Using Liposomes as Carriers," J. Clin. Pharmacol. 29:685–694 (1989).

Schafer-Korting et al., "Liposome preparations: A step forward in topical drug therapy for skin disease?," J. Am. Acad. Dermat. 21:1271–1275 (1989).

Seltzer, "The Role of Liposomes in Diagnostic Imaging," Radiology 171:19–21 (1989).

Yatvin et al., "Design of Liposomes for Enhanced Local Release of Drugs by Hyperthermia," Science 202:1290–1292 (Dec. 1978).

Yatvin et al., "pH-Sensitive Liposomes: Possible Clinical Implications," Science 210:1253–1255 (Dec. 1980).

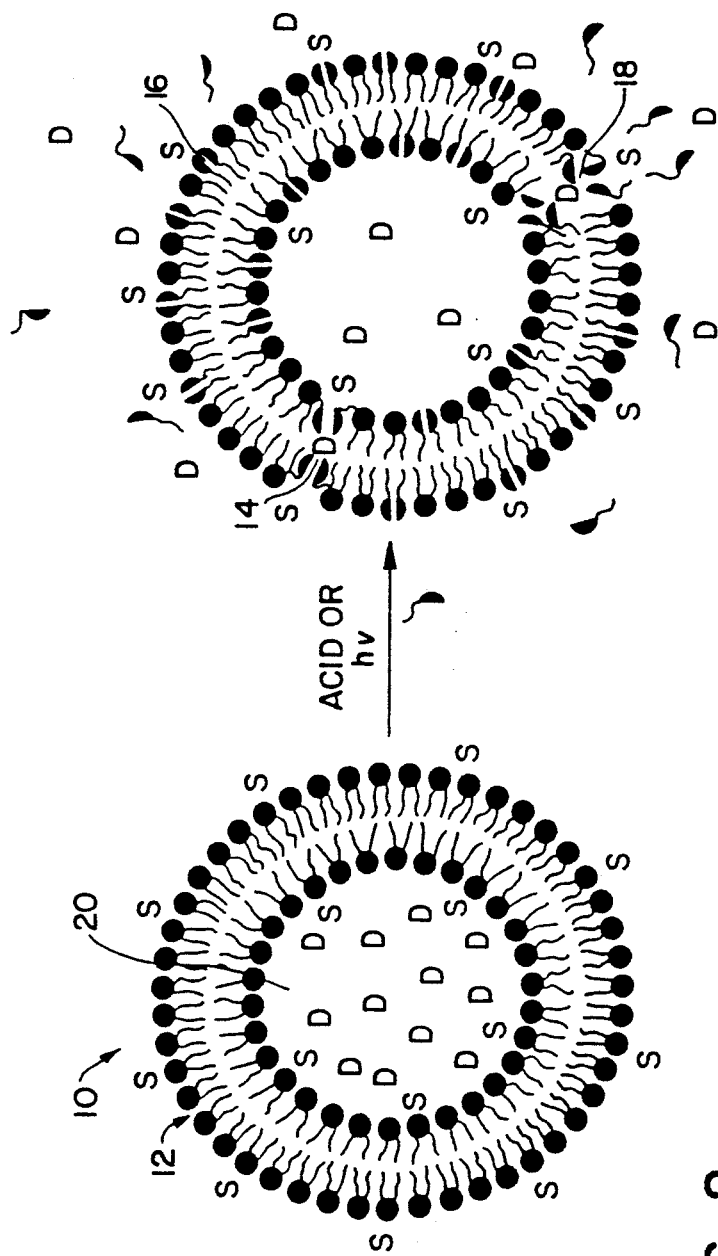
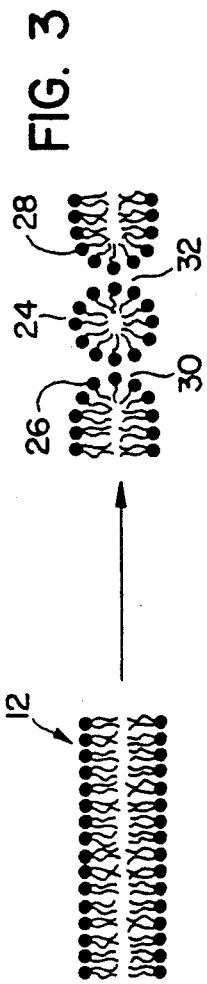
FIG. 2
FIG. 3

LIPOSOMAL DELIVERY SYSTEM WITH PHOTOACTIVATABLE TRIGGERED RELEASE

BACKGROUND OF THE INVENTION

1. Field of the Invention

This invention concerns liposomes, and more particularly liposomal delivery systems for transporting materials such as drugs, nucleic acids, and proteins. The liposomes selectively release their contents in response to an external triggering event, such as photoillumination.

2. General Discussion of the Background

Liposomes are microscopic lipid bilayer vesicles that enclose a cavity. The liposomal vesicles can contain a single bilayer (unilamellar vesicle) or multiple bilayers (multilamellar vesicle). These vesicles can encapsulate water-soluble drugs in their aqueous cavities, or carry lipid soluble drugs within the membrane itself. Liposomes have already been used for encapsulating therapeutic agents, such as cytotoxic drugs, and carrying them to biological target sites. For example, U.S. Pat. No. 3,993,754 discloses an improved chemotherapy method for treating malignant tumors in which an anti-tumor drug is encapsulated within liposomes and the liposomes are injected into an animal.

Encapsulation of pharmaceuticals in liposomes can reduce drug side effects, improve pharmacokinetics of delivery to a target site, and improve the therapeutic index of a drug. A serious limitation to the widespread use of liposomes, however, has been the difficulty of directing them to specific target sites. Liposomes administered intravenously to subjects are rapidly accumulated in the reticuloendothelial system. High liposome concentrations are thereby rapidly achieved in organs with fenestrated capillaries, such as the liver, spleen, and bone marrow. Liposomal systems can be effective in treating tumors that infiltrate these organs (such as hematologic malignancies), but have been less useful in treating targeted tumors in other anatomical locations. Previous research has investigated ways to "trigger" release from liposomes at other than reticuloendothelial target sites.

One prior approach has promoted leakage of liposome contents by heating a liposomal saturated target site above a critical temperature range, for example by radio frequency heating of target tissues. Yatvin et al., Science 202:1290 (1978). Another approach has used liposomes prepared from pH sensitive lipids, which leak their pharmaceutical contents into low pH target regions. Such areas of localized acidity are sometimes found in tumors, hence it has been proposed that intravenous administration of such liposomes would preferably selectively release anti-cancer chemotherapeutic agents at target tumors. Yatvin et al., Science 210:1253 (1980).

U.S. Pat. No. 4,882,164 similarly discloses a light sensitive liposome which undergoes a trans to cis isomerization upon irradiation with an appropriate wavelength of light (ultraviolet light) to allow the fluid contents of the liposome to escape through the membrane into the surrounding environment. Finally, GB Patent 2,209,468 discloses liposomes with an incorporated photosensitizing agent that absorbs light and alters the lipid membrane to release a drug from the liposome. Several reports of vesicle contents release using UV or visible light have appeared, but none of these systems have used biologically compatible lipids that are disrupted by light frequencies having tissue penetration depths exceeding 1 mm.

Photodynamic therapy (PDT) is another approach to treating localized areas of diseased tissue. A photosensitizer drug is administered systemically, topically, or by injection into a target site, such as a tumor. Illumination of the target site by an appropriate light source, such as an argon-pumped dye laser or sunlamp, induces a cytotoxic effect on the cells of the target site by one of two proposed mechanisms. In Type I photosensitization, the electronically excited drug reacts directly with a biological substrate, forming radicals which can initiate subsequent radical reactions that induce cytotoxic damage. Type II photosensitization involves energy transfer from the electronically excited drugs to oxygen, producing singlet molecular oxygen which subsequently produces cytotoxic oxygenated products.

Photodynamic therapy (PDT) has been used experimentally in cancer patients, and thousands of clinical trials are in progress throughout the world. One experimental drug known as Photofrin II (a purified version of hematoporphyrin derivative) is currently involved in randomized clinical trials. Other photosensitizing drugs used in photodynamic therapy procedures include phthalocyanines, merocyanine 540, substituted purines, xanthenes (Rhodamine 123 6G&B), cationic cyanine dyes, chlorine polymers, chalcogenapyrylium dyes containing selenium or tellurium atoms in the chromophore, phenothiazinium derivatives, benzophenoxoniums (Nile Blue A) and triarylmethanes (Victoria Blue BO [VB-BO]). Although remarkable results have been obtained in some PDT trials, several problems remain. Very high systemic doses of the sensitizer must often be given to achieve therapeutic levels at irradiated tumor sites, hence many sites in the body are nonselectively infiltrated by the sensitizer. The low solubility of some of the sensitizers reduces their usefulness for systemic administration because intravascular administration can provoke thromboembolic events.

Accordingly, it is an object of the present invention to provide an improved liposomal drug delivery system that is biocompatible and capable of triggered release of its contents.

Yet another object is to provide an improved liposome suitable for triggered release of its contents in response to alterations of pH.

Another object is to provide an improved liposomal triggered release system that reduces the effect of the triggering event on the drug carried by the liposome.

Yet another object is to provide an improved liposome suitable for use in photodynamic therapy.

Finally, it is an object of this invention to provide an improved method of photodynamic therapy which overcomes solubility problems with sensitizer drugs and is capable of delivering the drugs more selectively to a target site.

SUMMARY OF THE INVENTION

The foregoing objects are achieved, in one preferred embodiment, by providing an artificial liposome that includes a liposomal bilayer membrane enclosing a cavity. The liposomal membrane includes lipids containing a vinyl ether functionality which, when cleaved, produces a local disruption in the membrane. The liposome also contains a lysogenic substance, such as a photoactivatable dye, that cleaves the vinyl ether functionality in response to an external triggering event. The triggering event can be illumination with light, reduction in pH, or photoactivated reduction in pH by production of hydrogen ions.

In especially preferred embodiments, the membrane contains amphipathic lipids, preferably phospholipids, having a polar head group and two lipophilic chains that allow the lipid to pack into a bilayer structure. The lipophilic chains are preferably derived from fatty acids, and only one of the lipophilic chains contains the vinyl ether functionality. Other embodiments are possible in which both chains contain a vinyl ether functionality. A specific phospholipid that fulfills this requirement is a plasmalogen having the formula:

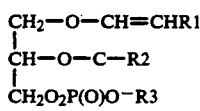

wherein $R_1$ and $R_2$ are each long hydrocarbon chains (or vinyl ethers), for example alkyl or alkenyl. In preferred embodiments, $R_1$ and $R_2$ are each $(CH_2)_n$ where n is 12-24 and $R_3$ is a bilayer forming phosphoryl ester, such as choline, ethanolamine, serine, or inositol. In particularly preferred embodiments, one of $R_1$ or $R_2$ is 12-16 carbons long, and the other chain is at least 16 carbons long, more preferably 18 carbons.

The lysogenic substance that cleaves the vinyl ether functionality preferably produces reactive oxygen species or acid in response to illumination of the lysogenic substance with light of a wavelength that is absorbed by the substance. The pharmaceutical, cosmetic, diagnostic or other substance delivered by the liposome can be carried in either the liposomal cavity or the lipid bilayer of the liposome. This versatility of location is advantageous because the liposome can be designed to carry the drug and lysogenic substance in different compartments. The drug can be carried in the enclosed cavity when the lysogenic substance is a lipophilic photosensitizer that will reside entirely or primarily in the bilayer membrane. Alternatively, lipophilic drugs can be carried in the bilayer when the photosensitizer is present in the cavity. This spatial separation of the photosensitizer and drug helps protect the drug from oxidation by reactive oxygen species or biological and/or physiochemical damage caused by a localized increase of acidity in response to illumination of the photosensitizer.

The present invention also includes a method of delivering therapeutic substances or cosmetics in liposomes to a target site in the subject. The liposomal membrane includes a lipid that contains the vinyl ether functionality which produces a local disruption in the membrane when the functionality is cleaved. A therapeutic or cosmetic substance is released from the liposomal cavity when a lysogenic substance carried by the liposome is illuminated with light. The light absorbed by the lysogenic substance cleaves the vinyl ether functionality to produce the local disruption in the membrane. In this manner, the therapeutic substance can escape from the liposome.

The liposomes are administered to a subject either intravenously, or by direct injection into or topical application on a target site. The target site is then illuminated to cleave the vinyl ether functionality and selectively control the release of the carried substance at the target site. The target site is preferably illuminated with light in the red or near infrared portion of the spectrum. The light preferably has a wavelength above about 640 nm, more preferably above 700 nm, and most preferably above about 800 nm, because at those frequencies the light will penetrate deeply into the tissue.

BRIEF DESCRIPTION OF THE DRAWINGS

FIGS. 2 and 3 are schematic views of a liposome of the present invention showing the development of localized areas of disruption in the membrane in response to acidification or illumination.

DESCRIPTION OF SEVERAL PREFERRED EMBODIMENTS

Figure 1:
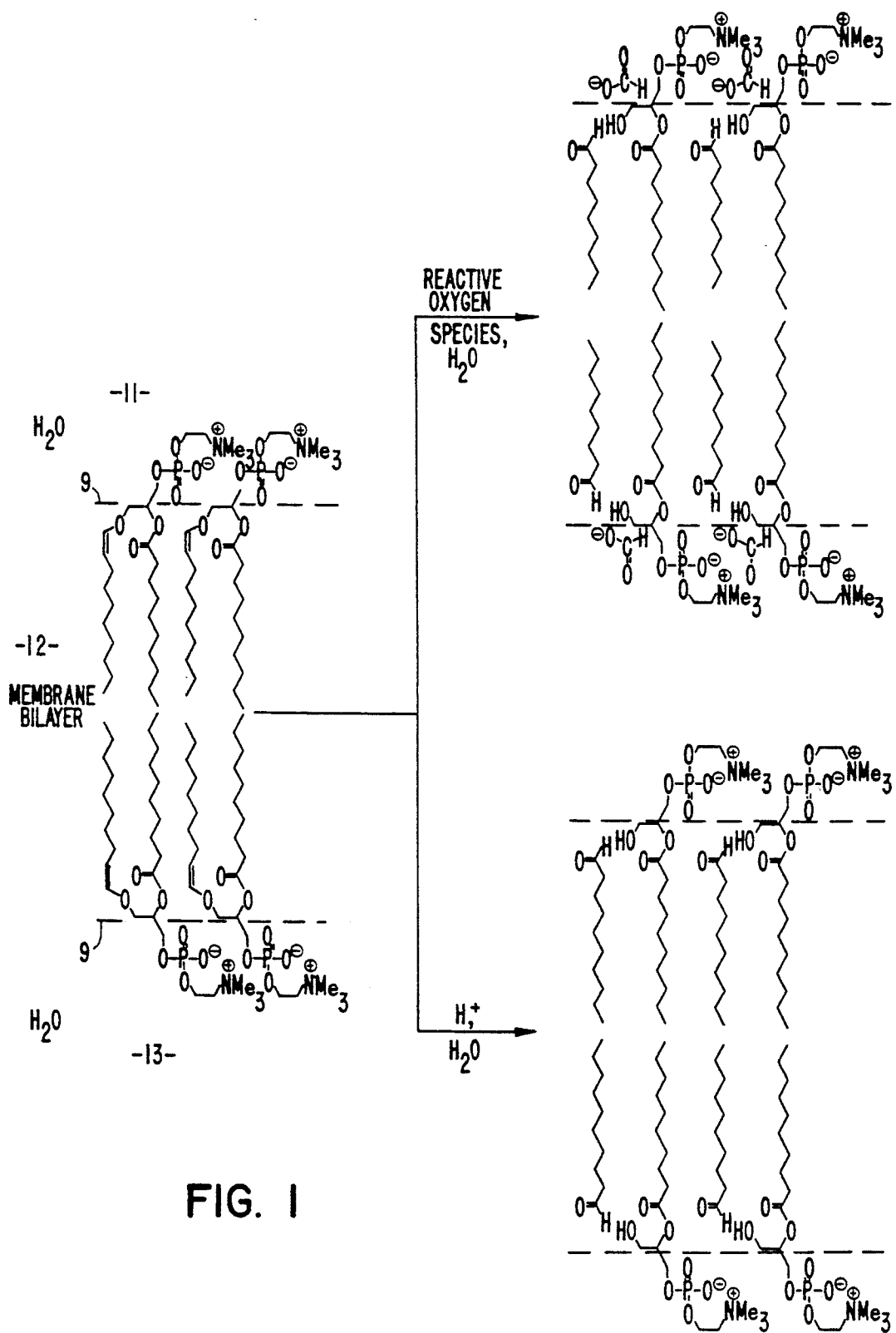
FIG. 1 is a schematic view of the reaction scheme for photolysis and acid catalyzed hydrolysis of the liposomal membrane of the delivery system of the present invention.

The present invention is a liposomal delivery system that transports a drug or other substances to target sites in a living organism, such as a human or animal. The liposome 10 (FIG. 2) is preferably a unilamellar bilayer membrane 12 containing an amphipathic phospholipid that contains the vinyl ether that is oxidized by reactive oxygen species (ROS) or hydrolyzed by acid. Acid hydrolysis can occur by direct reduction of pH in the environment of the liposome, or by use of a photoactivated sensitizer that releases acid in response to illumination. Cleavage of the vinyl ether group changes the lipid (as shown in FIG. 1) to create a local disruption in the membrane that allows a drug or other substance carried by the liposome to escape into the surrounding medium. An interface 9 between the membrane bilayer 12 and aqueous surrounding 11 or liposome interior 13 is shown by a dashed line in FIG. 1.

FIG. 2 shows that a lysogenic substance, such as a photosensitizer S, is carried in the liposomal cavity or membrane bilayer. When exposed to acid or light of an appropriate wavelength, the sensitizer (or direct acid exposure) induces breakage of the vinyl ether linkage. Cleavage of this functional group creates a local disruption, such as a pore 14 through the entire bilayer, a break 16 in the outer bilayer, or a disorganized area 18 through both the inner and outer portions of the bilayer. The local disruption can extend from a single pore or break, to a disorganized area, or even dissolution of the entire liposome, with release of its contents.

Although the inventors do not wish to be bound by theory, one conceptual mechanism for membrane disruption is shown in FIG. 3, where an isolated portion of the bilayer membrane 12 is shown before and after disruption. Prior to cleavage, the dialkyl amphiphiles tend to assume a cylindrical shape that produces a bilayer membrane. After cleavage, the monalkyl photoproduct kinetically prefers a cone shape, which tends to produce a micelle, such as micelle 24 between continuous membrane portions 26, 28. The micellar interruption may produce pores 30, 32 through which the contents of liposome 10 may pass.

The lysogenic photosensitizer triggers release or production of ROS or acid in response to photoillumination. Examples of photosensitizers that produce ROS in response to light include those shown in Table I below:

TABLE I

| Singlet Oxygen-Generating Sensitizers | | |
|---|---|---|
| COMPOUND | $\lambda_{max}(\log \epsilon)$ | $I(^1O_2)$ |
| Phenathiazinequinones: | | |
| 1 | 827(4.26); 748(4.2) | |
| 2 | 725(4.18); 665(4.08) | |
| 3 | 740(3.42); 667(3.43) | |
| 4 | 750(4.5); 685(4.26) | |
| Bis(2-ethyl-1,3'-dioxolane)kryptocyanine | 706(5.33) | <0.001 |
| Purpurins: | | |
| Octamethyl | 700(4.62) | 0.7 |
| Bacteriochlorophyll a | 780(4.95) | 0.3 |
| ZnPcS | 690(5.47) | |
| Phthalocyanines: | | |
| 2,9,16,23-Tetrahydroxy ZnPc | 684(5.0); 672(4.9) | <0.4 |
| 2,6,16,23-Tetrahydroxy Pc | 708(5.0); 672(4.9) | <0.4 |
| Sulfonated Naphthalocyanines (NcS): | | |
| AlClNcS | 770(5.3) | 0.3-0.4 |
| ZnNcS | 754(5.2); 732(4.8) | |
| SiNcS | 776(5.6) | 0.19 |
| Octaalkoxy Phthalocyanines: | | |
| ZnPc | 737(5.28); 661(4.6) | 0.47 |
| AlClPc | 764(5.3); 682(4.6) | 0.3 |
| GaPc | 767(5.3); 685(4.64) | 0.41 |
| SnPc | 779(5.3); 695(4.6) | 0.56 |
| H | 762(5.13); 740(sh) | |
| Clorins: | | |
| Bacteriochlorin a | 765(4.5) | |
| Tetrahydroxyphenyl bacteriochlorin | 741(4.95) | |
| Chlorin e | | |

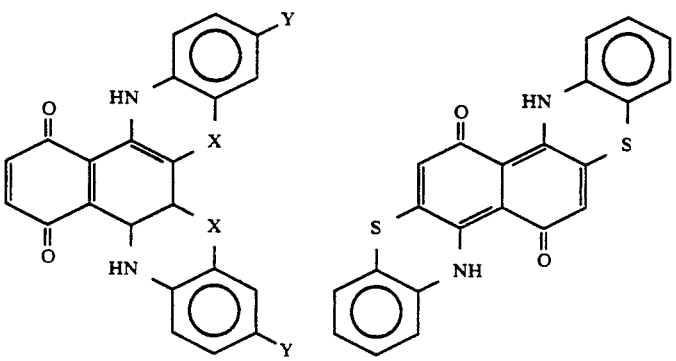

1  X = SO   Y = H
2  X = X    Y = H

TABLE I-continued

| | Singlet Oxygen-Generating Sensitizers | |
|---|---|---|
| COMPOUND | $\lambda_{max}(\log \epsilon)$ | $I(^1O_2)$ |
| 3  X = S   Y = OEt | | |

As used herein, the term reactive oxygen species includes, for example, singlet oxygen, hydroxyl radical, hydrogen peroxide and superoxide radical.

Examples of substances that reduce the pH in response to photoillumination include 4-formyl-6-methoxy-3-nitrophenoxyacetic acid (Janko, K.; Reichert, J. Biochim. Biophys. Acta 905:409-416 (1987)); triarylsulfonium salts (Dektar, J. L.; Hacker, N. P. J. Amer. Chem. Soc. 112:6004-6015 (1990)); dibenzenesulfonyldiazomethane and derivatives (Poot, A.; Delzenne, G.; Pollet, R.; Laridon, V. J. Photogr. Sci. 19:88 (1971)). The reaction mechanism for cleavage of the vinyl ether functionality is described in detail in Snyder, F., ed. "Ether Lipids: Chemistry and Biology," Academic Press, N.Y. (1972).

In the embodiment of FIG. 2, a liposomally transported drug D is encapsulated by liposome 10 and carried in a cavity 20 enclosed by the membrane 12. An aqueous or hydrophilic photoactivatable sensitizer S is carried in the aqueous cavity 20 and or the surrounding aqueous medium. After photoactivation of the sensitizer S, drug D is shown moving through the disruptions 14, 16, 18 in the membrane and escaping into the surrounding medium for transfer to the illuminated target area where delivery of the drug is desired. The drug D in FIG. 2 can be any water soluble or hydrophilic drug such as doxorubicin, daunomycin, or gentamicin that segregates wholly, predominantly or partially into the aqueous environment of the cavity 20. Alternatively, a hydrophobic drug is carried within or partially within the lipid hydrocarbon interior of membrane 12.

Hydrophobic drugs such as amphotericin B can be cosolubilized with lipid and carried primarily in the lipid bilayer membrane 12. See Lopez-Bernstein, J. Infect. Dis. 147:939-48, which is incorporated by reference, for a description of a method of making a liposome that carries amphotericin B. An alternative method for obtaining a high trapping efficiency in the lipid membrane is to chemically attach a hydrophobic group (e.g. a fatty acid or phospholipid) to the drug to create a molecule that is highly soluble in the liposome membrane.

In an alternative embodiment, the sensitizer and drug are carried separately in the cavity and lipid bilayer to minimize the effect of ROS or acid release from the sensitizer on the drug. In the amphotericin B liposomal carrier described above, a water soluble or hydrophilic photosensitizer such as AlClPcS is carried in the cavity 20 and surrounding aqueous environment. When a hydrophilic drug such as doxorubicin is carried in the liposome cavity 20, a hydrophobic sensitizer such as ZnPc is provided in the membrane 12.

The liposome of the present invention is preferably comprised entirely or partially of a phospholipid, such as a plasmalogen. A plasmalogen is a phospholipid that is present in platelets and liberates higher fatty aldehydes (e.g. palmital) on hydrolysis. Plasmalogens are also found in the cell membranes of muscle and the myelin sheath of nerve fibers. Examples of plasmalogens that are suitable in forming the liposomes of the present invention are derived from bovine heart phosphatidylcholine and bovine brain phosphatidylethanolamine. Plasmalogens are generally dialkylglycerols with two long-chain alkyl groups that may also contain one or more carbon-carbon double bonds. The plasmalogens of the present invention have a vinyl ether functionality at or near the interface 9 (FIG. 1) between the membrane bilayer and its adjacent environment 11 or aqueous core 13. The vinyl ether functionality should be within about 4 to 6 carbons of the interface 9, and most preferably at the interface (i.e. with no intervening carbons between interface and functionality). It is within the scope of this invention to provide additional double bonds in the fatty acid chain, preferably one or more double bonds that are conjugated with the double bond of the vinyl ether functionality.

A plasmalogen that has been used in developing the present invention is

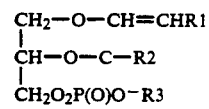

where $R_1$ and $R_2$ are each a long hydrocarbon chain. In preferred embodiments, $R_1$ and $R_2$ are each alkyl or alkenyl, preferably 12 to 24 carbons long. The $R_1$ or $R_2$ can, for example, be $(CH_2)_n$ where n is 12-24. Substituent $R_3$ can be:

$$-CH_2CH_2NH_2, -CH_2CH_2N + (CH_3)_3,$$
$$-CH_2CHNH_2COOH, -CH_2CHOHCH_2OH,$$

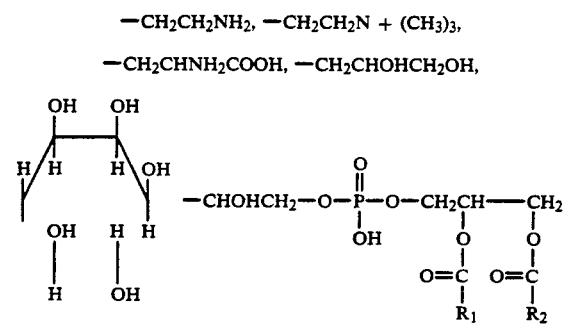

and

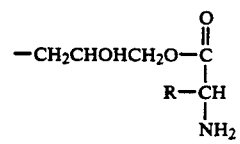

(where R, $R_1$, and $R_2$ represent alkyl groups).

When rapid triggered release of liposomal contents is desired, shorter $R_1$ and $R_2$ chains are preferred wherein n is 12-16. However, more stable particles with a lower background leakage rate are obtained with longer $R_1$ and $R_2$ chains wherein n is 18-24. The competing considerations of liposomal stability and rapid triggered release may be balanced by making one of $R_1$ or $R_2$ a short chain with n=12-16, and the other of $R_1$ and $R_2$ a longer chain with n=18-24. It is believed that such liposomes will have increased stability imparted by the longer R chain with reduced leakage of contents, yet rapid triggered release of liposomal contents imparted by the shorter R chain.

Either one or both of $R_1$ and $R_2$ can have a vinyl ether functionality.

Liposome Preparation

General methods of making liposomes are known. See for example U.S. Pat. No. 4,882,165, and Deamer and Uster, "Liposome Preparation: Methods and Mechanisms," in *Liposomes*, Marcel Dekkev, Inc., New York (1983), both of which are incorporated by reference. The general scheme used to make the specific embodiments of the liposomes of the present invention is to prepare a thin film of lipid by evaporation of a solvent. The dried lipid film is then mixed with the photosensitizer and carrier substance, warmed, vortexed, and either sonicated anaerobically or put through several freeze thaw cycles followed by extrusion through nucleopore filters to load the liposomes.

Loading Drugs Into Liposomes

Several methods by which drugs are loaded into liposomes are described in Ostro and Cullis, Am. J. Hosp. Pharm. 456:1576–1587 (1989) and by Juliano, "Interactions of Proteins and Drugs with Liposomes," in *Liposomes*, Ibid., which are both incorporated by reference. Most drugs are loaded at the time the liposome is formed by cosolubilizing the drug with the starting materials. The site of the liposome (cavity or membrane) into which the drug is located depends on the properties of the drug. A hydrophobic drug such as amphotericin B, for example, is cosolubilized with lipid in an organic solvent. See Lopez-Bernstein, J. Infect. Dis. 147:939–45 (1983). Subsequent removal of the solvent and subsequent hydration of the liposome yields a liposome drug complex with the hydrophobic drug primarily in the membrane.

Water soluble drugs can be sequestered in the liposome cavity by submitting liposomes to several cycles of freezing and thawing in an aqueous solution containing the drug, as described above under Liposomal Preparation. Finally, charged amphipathic drugs can be loaded into preformed liposomes using transmembrane pH gradients, as described in Bally et al., Biochem. Biophys. Acta 812:66–76 (1985).

Photodynamic Sensitizers

In selecting sensitizers, preference is given to sensitizers having a high extinction coefficient (intense absorption) at the wavelength of the light chosen for irradiation. Table I gives the wavelengths of maximum absorbance of numerous sensitizers. Once the $\lambda$ max is known, an irradiation source may be chosen that will illuminate the liposome with light of a wavelength that has the same or approximately the same $\lambda$ max. In devising a liposomal delivery system of the present invention, one may first want to consider the hydrophobicity or hydrophilicity of the drug. A sensitizer may then be chosen that has the opposite solubility in water or lipid. The choice of the sensitizer can then guide choice of an irradiation source having a wavelength that corresponds to the $\lambda$ max of the sensitizer.

Another desirable attribute that provides general guidance in selecting a preferred sensitizer is the quantum yield of the sensitizer, which measures the efficiency of the sensitizer in transferring photonic energy. When triggering is to be effected by ROS, a sensitizer may be preferred that has a high quantum yield in transferring energy to oxygen and exciting it. When triggering is to occur by pH reduction, a sensitizer may be preferred that has a high quantum yield for production of hydrogen ion (H+).

Addition of Membrane Stabilizers

The liposomes described in the following examples are both pure plasmalogen liposomes and mixed liposomes containing plasmalogens and a stabilizer such as DHC or DPPC. It is possible to prepare stable, substantially pure plasmalogen liposomes as long as the plasmalogen is substantially completely in the photoactivatable dialkyl amphiphile form. Inclusion of a significant amount of monoalkyl cleaved amphiphile photoproducts in the starting materials increases leakiness of the liposome. A substantially pure dialkyl amphiphile is defined as having less than 20% lysolipid by weight. It is especially preferred that the dialkyl have less than about 2% of the monoalkyl lysolipid by weight.

Liposomes that are not substantially pure can be stabilized by including co-lipids such as dihydrocholesterol (DHC) and dipalmitoyl phosphatidylcholine (DPPC), or by increasing alkyl chain length to include greater than about 16 carbons. Although there are no critical amounts of co-lipid beyond which membrane stabilization suddenly occurs, it has been found suitable to add about 10% or more by weight of the co-lipid.

Examples of other co-lipoid stabilizers that could be used would be sulfate, phosphate and glucosiduronate cholesterol derivatives (Cheltham et al., J. Biol. Chem. 265:12404–409 (1990)); ergosterol; dehydroergosterol (Kas et al., Biochemistry 29:1315–1322 (1990)); and tocopherol (Halks-Miller et al., Lipids 20:195–200 (1985)).

EXAMPLE I

Merocyanine 540 (MC-540) and chromatographically purified calcein were purchased from Molecular Probes, Inc. Palmitic anhydride from American Tokyo Kasei, N,N,N',N'-tetramethyl-phenylenediamine (TMPD), and 98+% zincpthalocyanine (ZnPc) from Aldrich Chemical Co. were used as received. DMAP (4-(di-methylamino) pyridine) from American Tokyo Kasei was recrystallized from ether. NADP, ATP, hexokinase, and glucose-6-phosphate dehydrogenase were purchased from Sigma Chemical Co. DPPC and BHPC (bovine heart phosphatidylcholine) were obtained from Avanti Polar Lipids, and showed single spots upon 1-dimensional silica TLC ($CHCl_3$/MeOH/$NH_4OH$; 65:35:6). All lipids were stored at $-20°$ C. under argon until use. $CHCl_3$ and benzene were dried over $P_2O_5$ and $CaH_2$, respectively, and distilled. Silica was pre-washed with 1:1 $CHCl_3$/MeOH and dried at 110° C. prior to use.

Steady-state absorption spectra were recorded on a Hewlett-Packard 8452A UV-vis diode array spectrophotometer. Differential scanning calorimetry (DSC) was performed using a Perkin Elmer DSC 7/Intercooler capable of subambient operation. Sample and reference were heated at 2°–5° C./min, typically from 5°–75° C. Fluorescence measurements were conducted on a Perkin Elmer MPF-66 fluorometer equipped with a thermostated sample compartment. $^1$H-NMR spectra were recorded on a General Electric QE-300 spectrometer with tetramethylsilane as internal standard. Light intensity at the irradiation cuvette surface was measured with a Coherent 210 power meter.

Preparation of 1-alk-1'-enyl-sn-glycero-3-phosphocholine (lysoPlasPC)

Lysoplasmenylcholine (1-alk-1'-enyl-sn-glycero-3-phosphocholine) was prepared by alkaline deacylation of BHPC (0.05N KOH in MeOH/benzene) and purified by flash chromatography on silica using sequential-step gradients of $CHCl_3$/MeOH (Bergelson, 1980). Yields ranged from 50-60%, based on plasmalogen content of the natural lipid source. The purified lysoplasmenylcholine was a single spot by TLC in $CHCl_3$/MeOH/$NH_4OH$ (65:35:7) and $CHCl_3$/MeOH/$H_2O$ (65:35:5).

Preparation of 1-alk-1'-enyl-2-palmitoyl-sn-glycero-3-phosphocholine (PlasPPC):

Lysoplasmenylcholine was acylated by minor modification of the procedure described by Guivisdalsky et al. J. Org. Chem. 54:4643–4648 (1989). Lysoplasmenylcholine (213 mg; 0.44 mmol), palmitic anhydride (917 mg; 1.9 mmol), and DMAP (60 mg; 0.49 mmol) were combined with 5 ml of $CHCl_3$ and stirred at room temperature under argon for 48 hours. The reaction mixture was filtered through a pad of Celite, and the solvent removed under reduced pressure. The crude material was dissolved in 95:5 $CHCl_3$/MeOH and purified by silica gel flash chromatography using sequential-step gradients of $CHCl_3$/MeOH (95:5, 90:10, 80:20, and 30:20) to give PlasPPC (274 mg, 87%) that was one spot by TLC ($R_f$=0.52 in $CHCl_3$/MeOH/$NH_4OH$, 65:35:6). $^1$H-NMR ($CDCl_3$): 5.91 (d, J=6.16 Hz, 1 H, —OCH=C—), 5.34–5.14 (m, 1.65 H, vinyl H and O—C=CH), 4.42–4.32 (m, 3 H, sn-2 CH and $POCH_2$), 4.02–3.78 (m, 4 H, sn-1 $3CH_2$), 3.5 (s, 2 H, $NCH_2$), 3.38 (s, 9 H, $N(CH_3)_3$), 2.24 (t, J=7.48 Hz, 2 H,–$OCOCH_2$), 2.02 (m, 2 H, allelic $CH_2$), 1.28 (m, 49–50 H), 0.9 (t, 6H, ω—$CH_3$).

Photoinduced Release

PlasPPC/DPPC (8:1 mol/mol) vesicles for photodynamic studies were prepared by dissolving dry lipids in chloroform and removing the solvent with a stream of argon. The resultant lipid film was then dried under vacuum for 1–2 hours to remove entrapped solvent. An ethanolic stock solution of ZnPc was prepared by dilution from a 5 mM pyridine solution of the sensitizer. Then, 100–200 μl of the ethanolic ZnPC was added to 2.8 ml of 20 mM Tris, pH 8, containing 165 mg of glucose (~0.3 M). The suspension was warmed to 45° C., vortexed, and put through five freeze-thaw cycles with the liposomes. Finally, the suspension was extruded ten times through stacked 0.08-micron Nucleopore filters using a Lipex Biomembranes Extruder thermostated at 47° C. Unentrapped sensitizer and glucose were removed by passage down a small buffer-equilibrated Sephadex G-25 column. UV-vis analysis (after solubilization with 10% Triton X-100) and phosphorus assay as described by Petitou, Anal. Biochem. 91:350–53 (1978) indicated that the concentration of ZnPc and lipid in these vesicles was 0.05–0.1 μM and 4.8 mM, respectively.

MC-540 was incorporated into PlasPPC/DPPC liposomes in a similar manner except that the sensitizer was dissolved directly in the glucose/Tris solution before addition to the lipid film. Final concentration of MC-540 was 20 μM, as determined spectrophotometrically.

Stirred, thermostated (±0.1° C.) solutions of MC-540-containing liposomes were irradiated using a 100-W tungsten lamp (10 mW/cm$^2$) filtered through a 10-cm water cell and a Corning OG-495 filter. ZnPc liposomes were irradiated with a 1600-W high-pressure xenon lamp (Osram XBO-1600). The incident beam (80 mW/cm$^2$) was passed through a 10-cm cell through which flowed a cooled 0.–02% rhodamine B (aq) solution. This solution filter allowed passage of light of wavelength greater than 640 nm (Parker, 1968). The temperature inside the photolysis cell was monitored periodically with a calibrated Fluke 51 K/J thermocouple. By this method, it was determined that the temperature of the illuminated sample did not vary by more than 0.2° C. over the course of the experiment.

Contents leakage was monitored by withdrawing 25 to 50-μL aliquots of liposomal solution at various times during the course of photolysis. Glucose leakage was analyzed by the glucose oxidase assay of Demel et al., Biochem. Biophys. Acta. 150:655–665 (1968); and Kinsky et al., Biochem. Biophys. Acta. 152:174–185 (1968).

Lipid Peroxidation

Hydroperoxide formation was examined by thin layer chromatography with slight modification of the procedure reported by Girotti et al., Arch. Biochem. Biophys. 236:238–251 (1985). All manipulations were conducted under dim room lights. Following extraction with 2:1 (v/v) $CHCl_3$/MeOH, the lipids were spotted on Baker silica IB-F plates and developed in 75:25:4 (v/v/v) $CHCl_3$MeOH/$H_2O$. The plates were then dried and sprayed with 1% TMPD in 1:1 (v/v) $CHCl_3$MeOH containing 1% acetic acid. Under these conditions, PlasPPC had an $R_f$ of 0.32 with the oxidized product appearing as a purple spot at $R_f$ 0.24.

pH-Induced Release

Liposomes for pH-triggered release studies were prepared as described above. In a typical experiment, 4 mg of PlasPPC and 0.7 mg of DPPC were combined with 1 ml of $CHCl_3$, dried under vacuum, and combined with 2.5 ml of 20 mM Tris containing 46.8 mg of calcein. Following adjustment of the pH to 8 with 5N NaOH, the vortexed suspension was put through five freeze-thaw cycles. Liposomes were extruded five times through two stacked 0.1-micron Nucleopore filters as before. Liposomes (50 ||1) were collected from a G-25 column and diluted with 1.45 ml of 20 mM NaOAc/HOAc+30 mM NaCl, pH 4.2 buffer or with the same volume of 20 mM Tris+30 mM NaCl, pH 8 buffer. Release of calcein was monitored as described by Allen in Liposome Technology (edited by Gregoriadis), Vol. 3 at 177–182, CRC Press, Boca Raton, Fla. (1984). The percentage of release was calculated following disruption with 100 μl of 10% Triton X-100.

Differential Scanning Calorimetry

Table II gives the main gel-to-liquid crystalline phase transition temperature, $T_c$, of DPPC and PlasPPC liposomes (<1000 Å), as well as the $T_c$ of liposomes containing the two lipids in varying molar ratios.

TABLE II

| Calorimetric Data for Plasmalogen Liposomes | |
|---|---|
| Composition[a] | $T_c$ (°C.)[b] |
| PlasPPC | 39.4 |
| DPPC | 41.5[c] |

TABLE II-continued

| Calorimetric Data for Plasmalogen Liposomes | |
|---|---|
| Composition[a] | $T_c$ (°C.)[b] |
| PlaPPC/DPPC[d] (8:1) | 38.5 |
| Plas/DPPC[e] (8:1) | 38.9 |
| PlasPPC/DPPC (1:1) | 39.4, 43.4 |
| PlasPPC/DHC (30 mol % DHC) | 46.5 |

[a]10 mM lipid in 20 mM Tris buffer, pH 8; <1000 Å diameter
[b]±1° C.
[c]cf. 41.4° C. (Blume (1983) and Lentz et al. (1987))
[d]Contains <1 μM ZnPc + 0.3M glucose
[e]Contains 0.3M glucose PlasPPC and 8:1 PlasPPC/DPPC exhibit a single, broad transition with width at half-maximum of ~5° C. Such broad, noncooperative transitions may be attributed to the dispersity of molecular species which comprise the semi-synthetic liposomes. It has been shown by Creer and Gross, J. Chromatogr. 338:61-69 (1985) that in the absence of further chromatographic separation, preparation of PlasPPC by the method described above results in a mixture of 1-alk-1'-enyl lipid chains of which 96% are saturated, with 68% being $C_{16:0}$.

Table II also gives the $T_c$ for a representative sample of PlasPPC containing <1 μM lipophilic ZnPc and/or 0.3M glucose entrapped within the aqueous core of the vesicles prior to photolysis. Comparison of these data with those from unloaded PlasPPC liposomes indicates that molecular packing is not perturbed appreciably upon incorporation of sensitizer and glucose within the hydrocarbon and headgroup regions of the liposome Photosensitized Disruption of Liposomes The disruption of plasmalogen containing liposomes by irradiation with light was studied in liposomal systems that contained a ZnPc photosensitizer that produced ROS in response to irradiation. The liposomes were irradiated with the 1600 W high pressure xenon lamp for the period of time indicated on the horizontal axis of the Figures discussed below.

Figure 4:
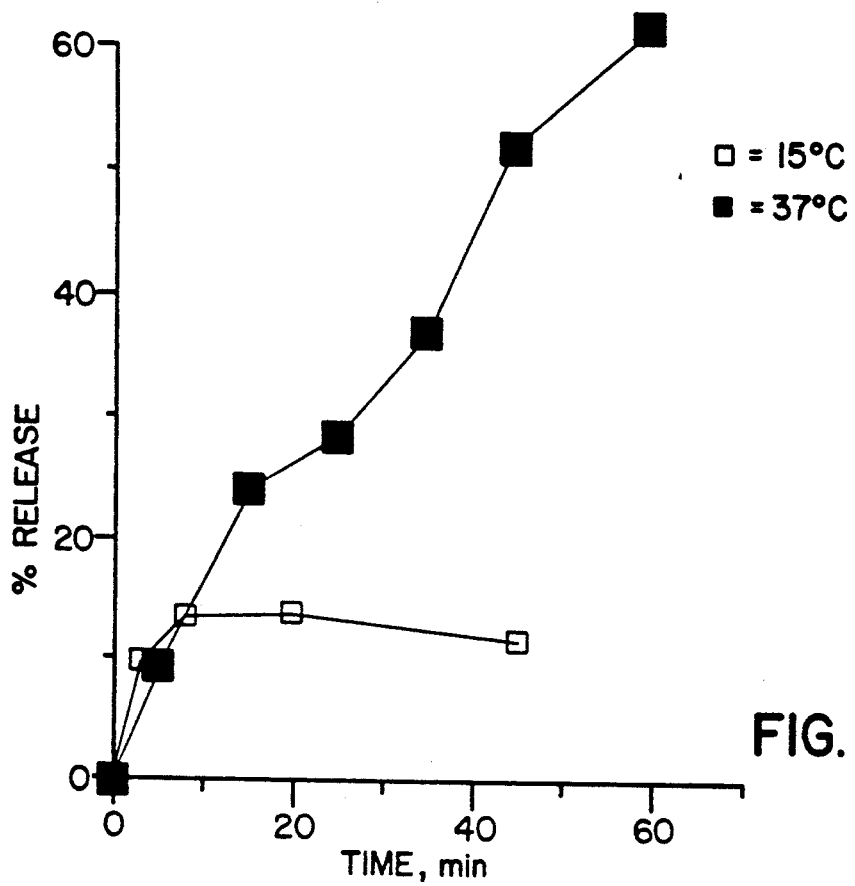
FIG. 4 is a graph showing ZnPc-sensitized release of glucose from PlasPPC/DPPC at 15° C. (□) and at 37° C. (■).

FIG. 4 shows the release kinetics of liposome entrapped glucose after irradiation of 8:1 PlasPPC/DPPC liposomes containing ZnPc as the photosensitizer ([lipid]/[ZnPc]>10^4). Release rates were determined at 15° C., at which temperature the vesicles are in the gel phase, and at 37° C., where a more fluid bilayer predominates. After 60 minutes of irradiation, less than 20% of the entrapped glucose has been released at 15° C., compared with 62% at 37° C. Photoirradiation of the liposomes therefore enhances glucose release at the physiological temperature of 37° C. which is found in a human body. Dark leakage from ZnPc/PlasPPC/DPPC liposomes was also measured at both temperatures. After 60 minutes at 15° and 37° C., glucose release was found to be 4 and 30%, respectively. Hence, irradiation of the liposomes produces a substantial increase in glucose release of the ZnPC/PlasPPC/DPPC vesicles.

Figure 5:
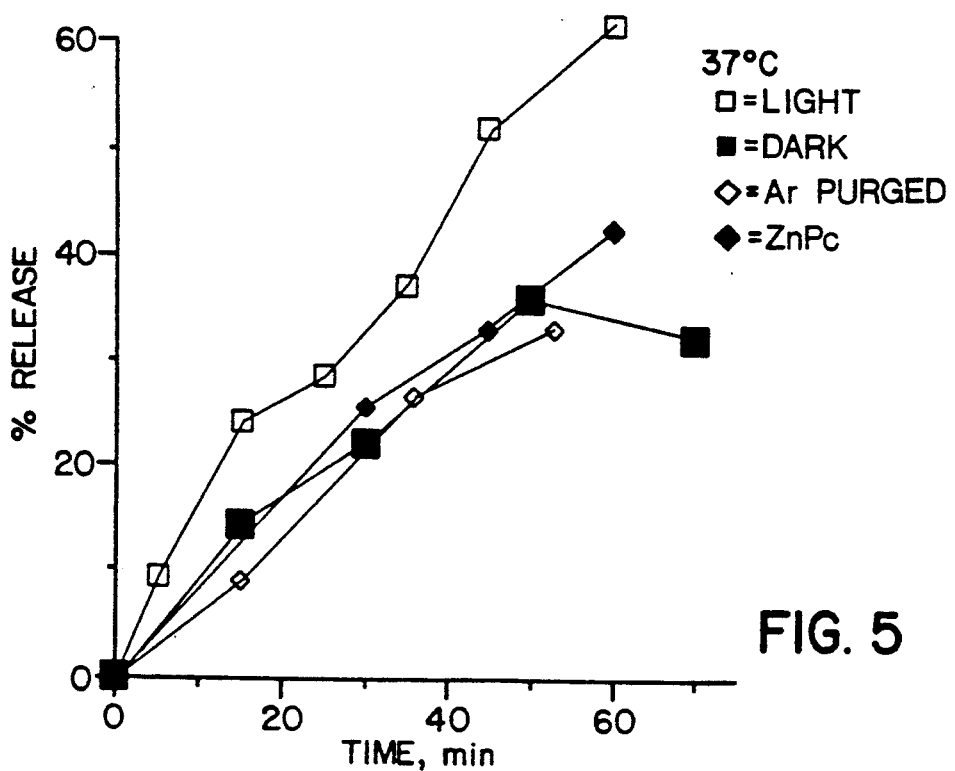
FIG. 5 is a graph showing ZnPc-sensitized release of glucose at 37° C. from PlasPPC/DPPC liposomes with near red light λ>640 nm (□); in the dark (■); argon-purged (◇); and in a liposome without a ZnPc lysogenic sensitizer (◆).

Photoinduced release rates at 37° C. are shown in FIG. 5 along with those for various control experiments. Irradiation of liposomes in the absence of ZnPc or following argon purging of the suspensions results in release rates indistinguishable from dark (thermal) leakage rates. Irradiation of pure DPPC vesicles at their $T_c$ under identical conditions of sensitizer and oxygen used in FIG. 4 (8:1 PlasPPC/DPPC) resulted in leakage rates similar to those measured in a dark DPPC control (data not shown).

TLC analysis of PlasPPC/DPPC/ZnPc irradiated samples indicates the formation of a new product with slightly lower $R_f$ than PlasPPC. This spot stained dark blue with N,N,N',N'-tetramethylphenylenediamine spray reagent, suggesting that the oxidized lipid product is a hydroperoxide. No hydroperoxide product was observed in dark, sensitizer-free, or argon-purged controls.

Possible involvement of singlet oxygen ($^1O_2$) in this system was studied by irradiating an identical liposome preparation containing 100 mM sodium azide, a known $^1O_2$ quencher. No protection against vesicle lysis was afforded by azide in these experiments (FIG. 5).

Acid-Triggered Release of Calcein

Figure 6:
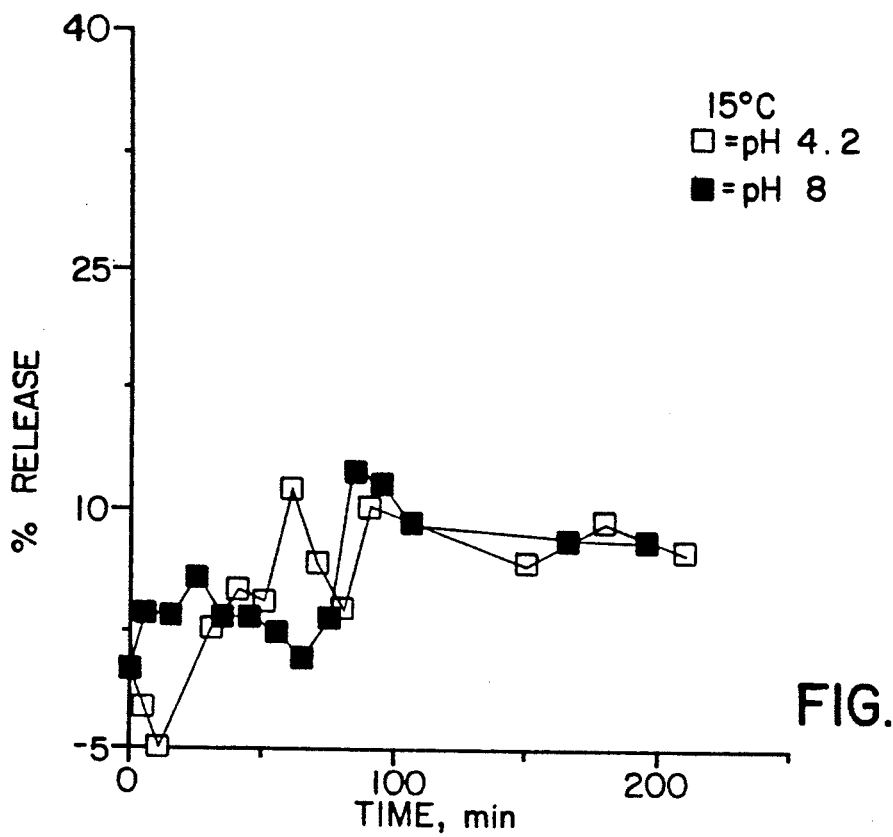
FIG. 6 is a graph showing the percentage of acid-triggered release of calcein from PlasPPC/DPPC liposomes at 15° C. and pH 8 (■); and pH 4.2 (□).
Figure 7:
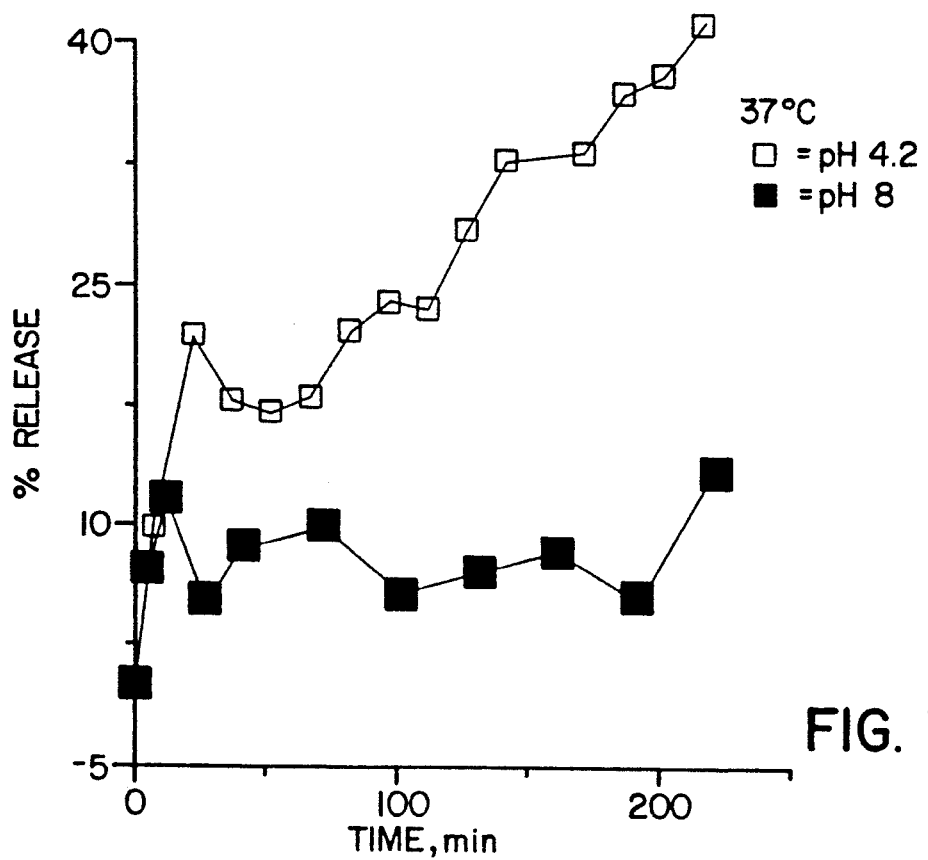
FIG. 7 is a graph showing the percentage of acid-triggered release of calcein from plasPPC/DPPC liposomes at 37° C. and pH 8 (■) and pH 4.2 (□).

Release of calcein from PlasPPC/DPPC liposomes leads to an increase in fluorescence intensity. FIG. 6 shows the time courses of release at 15° C. at pH 8 and 4.2. The analogous plot at 37° C. is given in FIG. 7. While release rates of calcein at 15° C. appear to be independent of pH, a substantially increased rate is observed at the physiological temperature of 37° C. Thus, after 3 hours, 37% of the calcein has been released at pH 4.2, whereas only 7% has leaked out of the liposomal core at pH 8.

While the type II production of singlet $O_2$ is thought to be the predominant mechanism in many photodynamic sensitizations, the type I free radical pathway can become important under certain conditions. These include membrane binding of the sensitizer, high lipid/oxygen ratios in the immediate environment of the sensitizer, and high light intensity. When added to PC liposomes, ZnPc is thought to be localized in the hydrophobic bilayer interior. The inventors also believe that the ZnPc dye is similarly incorporated into the bilayer of plasmenycholine liposomes such that the local concentration of lipid is high. Hence, the type I pathway may play an important role in ZnPc sensitization of the liposomes of the present invention.

The observation that azide does not decrease the photostimulated leakage of glucose suggests that $^1O_2$ is not responsible for the formation of lipid peroxides observed by TLC. Lipid peroxidation in this system appears to involve radical oxygen species other than singlet oxygen generated via excited-state ZnPc.

The results shown in FIG. 5 indicate that irradiation of ZnPc at 37° C. causes glucose to be released at a rate significantly above the dark leakage rate in a PlasPPC/DPPC liposome. TLC data suggest qualitatively that one of the products formed upon photolysis results from oxidation of the vinyl ether-containing chain. Therefore, disruption of the PlasPPC bilayer via this photooxidation then results in leakage of contents into the surrounding medium as shown in FIGS. 1 and 2. However, release rates measured during irradiation in the gel phase of PlasPPC/DPPC are more similar to both ZnPc- and MC-540-containing liposomes from non-irradiated samples. This suggests that increased vesicle release rates occur when the bilayer is in the more fluid liquid crystalline phase. Increased viscosity of the gel phase and decreased oxygen solubility below $T_c$ may both contribute to this effect. Hence the liposomes of the present invention have the advantage of performing their intended leakage function better at physiological temperatures.

No analogous glucose release effect was observed in irradiated pure DPPC liposomes with a ZnPc sensitizer (data not shown).

Acid-Triggered Release

Acid hydrolysis of the sn-1 vinyl ether linkage of plasmalogens results in the formation of fatty aldehyde and lysolipid, as shown in Eq. 1 below. The data in FIGS. 6 and 7 demonstrate that hydrolysis at pH 4.2 results in release of contents from the aqueous core, consistent with a destabilization of the vesicle at low pH. As noted for the photosensitized release, less release was observed at this pH when the solution temperature was below $T_c$.

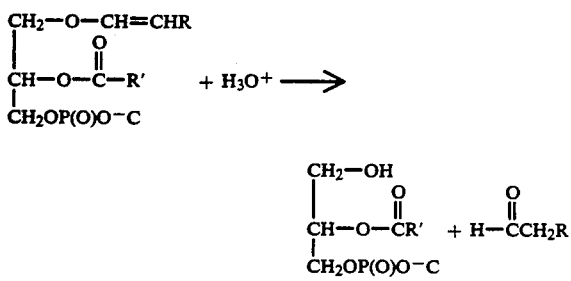

A significant advantage of the present invention is that the transition temperature of PlasPPC is within a degree of physiological temperature. At similar light fluxes, the in vivo kinetic release profiles using ZnPc within the liposome should be similar to those shown in FIGS. 4 and 5. While some thermal leakage occurs at 37° C., PlasPPC-based liposomal systems are suited for use as drug delivery systems.

Stimulated release of encapsulated materials from plasmalogen liposomes triggered by visible light or acidification has been demonstrated in this Example. The liposome delivery system in this Example includes the naturally occurring 1-alk-1'-enyl-2-acyl-sn-glycero-3-phosphocholines which in the presence of light, $O_2$, and sensitizer photooxidize the phospholipid with reactive oxygen species such as radical oxygen and/or $^1O_2$ intermediates. Hydrophilic agents such as glucose are released by photooxidation from these liposomes.

EXAMPLE II

This Example describes the use of AlClPcS sensitizer, a water-soluble phthalocyanine localizing in the aqueous core of the vesicle, to produce photomodifications of plasmalogen liposomes via photodynamic mechanisms. The structural formula of the photosensitizer AlClPcS used in this study is shown below.

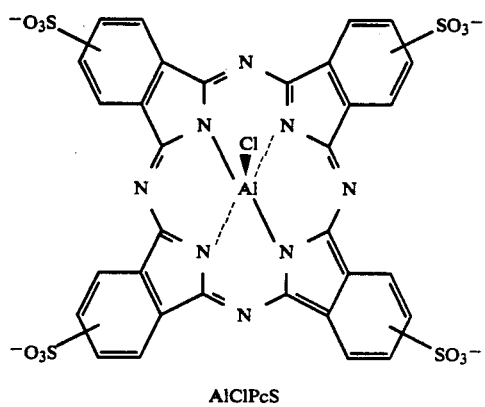

AlClPcS

Melting points were measured on Mel-Temp II capillary melting point apparatus and are corrected. AlClPcS (Midcentury, Chicago, Ill.), and palmitic anhydride (American Tokyo Kasei) were used as received. NADP, ATP, hexokinase, Bakers yeast glucose-6 phosphate dehydrogenase, and D-glucose were obtained from Sigma. Dihydrocholesterol (DHC; Aldrich, m.p. 144°-5° C. m.p. 140°-142° C.)), 1,2-dipalmitoyl-sn-glycero-3-phosphocholine (DPPC; Avanti) and bovine heart phosphocholine (BHPC; Avanti) were single spots by silica TLC (DHC: 90:10 $CH_2Cl_2$/MeOH; DPPC and BHPC: 65:35:6 $CHCl_3$/MeH/$NH_4OH$) and were used without further purification. 1-alk-1'-enyl-2-palmitoyl-sn-glycero-3-phosphocholine (PlasPPC) was prepared by alkylation of 1-alk-1'-enyl-sn-glycero-3-phosphocholine following alkaline deacylation of BHPC. See Guisvisdalsky and Bittman, J. Org. Chem. 54:4643–48 (1989). Lipids were stored at −70° C. under argon until use. $CHCl_3$ was dried over $P_2O_5$ and freshly distilled prior to use. Silica for column chromatography was pre-washed in 1:1 $CHCl_3$/MeOH and dried at 110° C.

Steady-state absorption measurements and differential scanning calorimetry measurements were performed with the same equipment as in Example I. Samples were typically heated by 2°-5° C./min over the appropriate temperature range. Samples for electron microscopy were prepared by coating copper grids with extruded liposomes and staining with 2% ammonium molybdate in 20 mM Tris buffer, pH 8. Samples were vacuum dried for 3 hours and then visualized by transmission electron microscopy.

PlasPPC liposomes were prepared as 10 mM liposome suspensions by dissolving appropriate amounts of PlasPPC and either DHC or DPPC in 1-2 mL $CHCl_3$ and evaporating to a dry film using a stream of Ar. Following complete solvent removal under high vacuum for 1-2 hours, 3 ml of 20 mM Tris 100 mM NaCl buffer, pH 8, containing 0.3M glucose and 200-250 μL of 40 μM stock AlClPcS solution was added. This mixture was extensively vortexed at 55°-60° C., resulting in a pale blue suspension that was hydrated fully via five freeze-thaw cycles. The emulsion was then extruded ten times through stacked 1000 and 800 A Nucleopore filters at 48° C. using a thermostated Lipex Biomembranes Extruder. Unentrapped sensitizer and glucose were removed via gel filtration on a buffer-equilibrated Sephadex G-25 column. Concentration of AlClPcS in the final liposome suspension varied from 3-7 μM.

Experiments requiring the use of $NaN_3$ or $D_2O$ within the liposomes were prepared in the same manner. The pH of the buffer was adjusted to 8.4 using an Orion SA 720 pH meter (pD=pH+0.4) and DCl. All manipulations of sensitizer-incorporated liposomes were conducted in the dark or under reduced lighting conditions.

Photoinduced glucose release from the AlClPcS sensitized liposomes was shown by irradiating stirred, thermostated solutions of liposomes with a 100 W tungsten lamp whose output was first filtered through a 10 cm cell of water, followed by a Corning OG-630 cut-off filter, and then focused to fill a 1.5×0.5 cm² area of a standard 3 mL cuvette. Light intensity at the cuvette surface was measured with a Coherent 210 power meter and found to be 20 (±5) mW/cm². The temperature inside the photolysis cell was monitored periodically with a calibrated Fluke 51 K/J thermocouple and found to be constant to within ±0.2° C.

Leakage of liposomal contents at 37° C. was monitored by withdrawing 25 μL of liposomal solution at various times during the course of the photolysis. Released glucose was quantitated using the enzymatic glucose oxidase assay which involves monitoring production of NADPH ($\lambda_{max}$340 nm) that occurs by reduction of NADP during the enzymatic phosphorylation of released glucose. The total amount of entrapped glucose was determined following disruption of liposomes with Triton X-100 detergent.

Thin layer chromatography (TLC) was performed by adding 75 μL of liposomes to 150 μL of 2:1 CHCl$_3$/MeOH and vortexed to mix. The organic layer was removed, spotted on Baker silica 1B-F plates, and developed in 65:35:6 (v/v/v) CHCl$_3$/MeOH/NH$_4$OH. Spots were visualized after charring plates dipped in 20% H$_2$SO$_4$.

Table II gives the main gel-to-liquid crystalline transition temperature ($T_c$) of DPPC, PlasPPC, and mixed PlasPPC/DPPC or PlasPPC/DHC liposomes obtained by differential scanning calorimetry.

Pure PlasPPC liposomes show a $T_c$ slightly lower than that observed for the diacyl analogue, DPPC. Secondly, addition of DPPC (12 mol %) has little effect on $T_c$ of PlasPPC liposomes. Apparently, the structural similarity of DPPC and PlasPPC precludes any calorimetrically discernible regions of immiscibility (i.e., phase-separated domains) of the two lipids. In contrast, 30 mol % DHC increases the transition temperature by 7° C. This result is consistent with reported increases in $T_c$ for DPPC:30 mol % cholesterol mixtures of 5°–10° C. Incorporation of 30 mol % DHC reduced the magnitude and broadened the PlasPPC transition, making the transition unobservable in some samples.

Incorporation of glucose and AlClPcS at the concentrations used here did not result in significant variations in $T_c$ from that measured in unloaded vesicles, therefore, macroscopic molecular packing is not appreciably disturbed by solubilization of glucose and sensitizer within the core.

Encapsulation of AlClPcS in 800 Å diameter PlasPPC liposomes resulted in a small shift of the absorption maximum from 674 nm (20 mM Tris, pH 8; lit. maximum 675 nm (27)) to 672 nm. Absence of a large absorption maximum shift in liposomal solution is consistent with localization of AlClPcS predominantly in the interior aqueous core of the vesicles where interactions with the hydrocarbon bilayer of the liposome are minimal. Dye photobleaching was checked by monitoring the optical density at $\lambda_{max}$ throughout the course of the irradiation and/or measuring Triton X-100-disrupted aliquots of the liposomal solution. No bleaching of the AlClPcS was observed.

Figure 8:
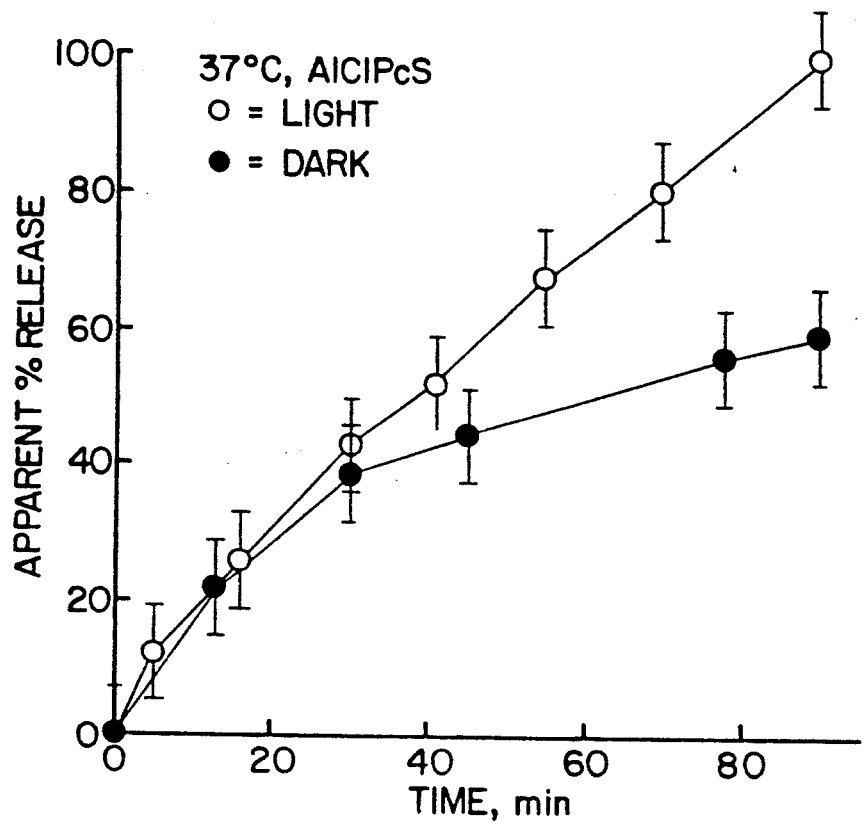
FIG. 8 is a graph showing the apparent percentage release of glucose from AlClPcS-sensitized PlasPPC/DPPC liposomes at 37° C. after irradiation with light having a wavelength greater than 630 nm (○); and in the absence of any photoirradiation (●).

FIG. 8 shows the photoinduced release kinetics of glucose from 10 mol % PlasPPC/DPPC liposomes at 37° C. loaded with AlClPcS ([lipid]/[AlClPcS] ca. 10$^3$). While release of entrapped glucose is essentially complete within 90 minutes of irradiation, permeation of glucose due to thermal processes results in release of 60% of the entrapped glucose in the absence of light during the same time interval. This high dark leakage rate was due to the presence of already oxidized vinyl ether linkages in the plasmalogen liposomes.

Figure 9:
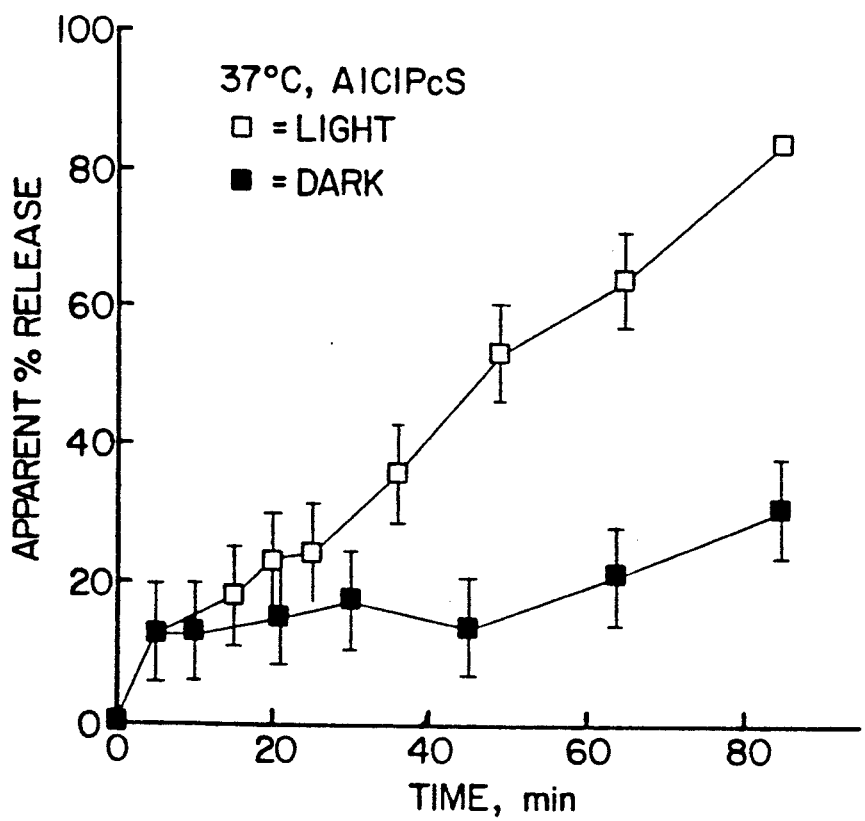
FIG. 9 is a graph similar to FIG. 8 showing the apparent AlClPcS-sensitized release of glucose from PlasPPC/DHC at 37° C. after irradiation with light having a wavelength above 630 nm (□); and in the dark with no photoirradiation (■).

PlasPPC liposomes containing DHC as co-additive were prepared in an attempt to reduce further the dark leakage rate of glucose from the PlasPPC/DPPC system that contained oxidized plasmalogen contaminants. Glucose release from these PlasPPC/DHC vesicles is plotted in FIG. 9. Photoinduced release rates from PlasPPC/DHC are within experimental error of those observed in PlasPPC/DPPC liposomes. After 90 minutes of dark permeation, however, only 25% of the entrapped glucose has been released from the PlasPPC/DHC liposome core, a 2.4-fold decrease from the PlasPPC/DPPC dark leakage rate. Hence, DHC appears to be a preferred colipid stabilizer in preparations using the AlClPcS water soluble sensitizer wherein significant amounts of lysolipid are present in the plasmalogen.

Figure 10:
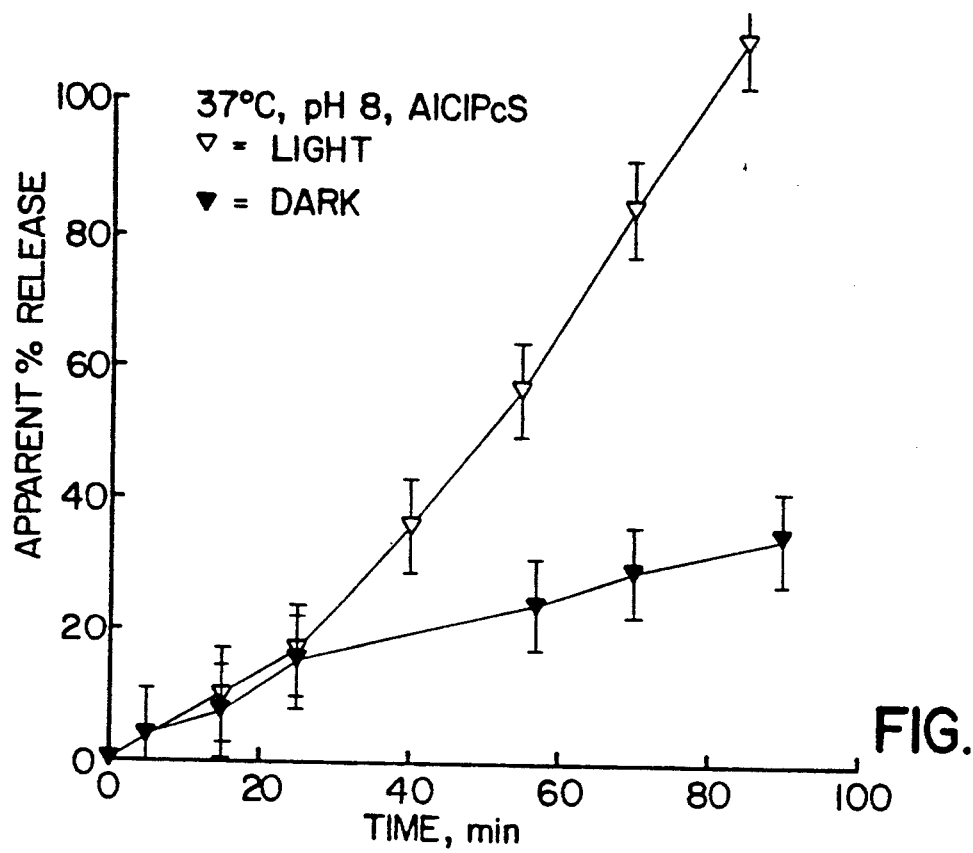
FIG. 10 is a graph illustrating lack of singlet oxygen intermediacy in AlClPcS-sensitized glucose release from PlasPPC/DHC (30 mol %) liposomes in 20 mM Tris/100 mM NaN$_3$, pH 8 at 37° C. as a function of time after irradiation (▽); and in the dark (▼).

Release rates monitored in the presence of 100 mM sodium azide, a known quencher of $^1O_2$, are shown in FIG. 10. Azide-containing liposomes exhibited a pronounced induction period (i.e., little measurable glucose release) during the first 25–30 minutes of irradiation compared with the azide-free control (compare FIGS. 9 and 10). This result is consistent with azide quenching of a pathway responsible for short-time modification of liposome properties on a short timescale. UV/Vis analysis before and after 90 minutes of photolysis indicated a slight increase in optical density at 672 nm from 0.454 to 0.567. Although processes responsible for damaging liposomal integrity are quenched at early times, 90 minutes of irradiation results in some changes in the light scattering properties of the liposomes even in the azide-containing sample.

Figure 11:
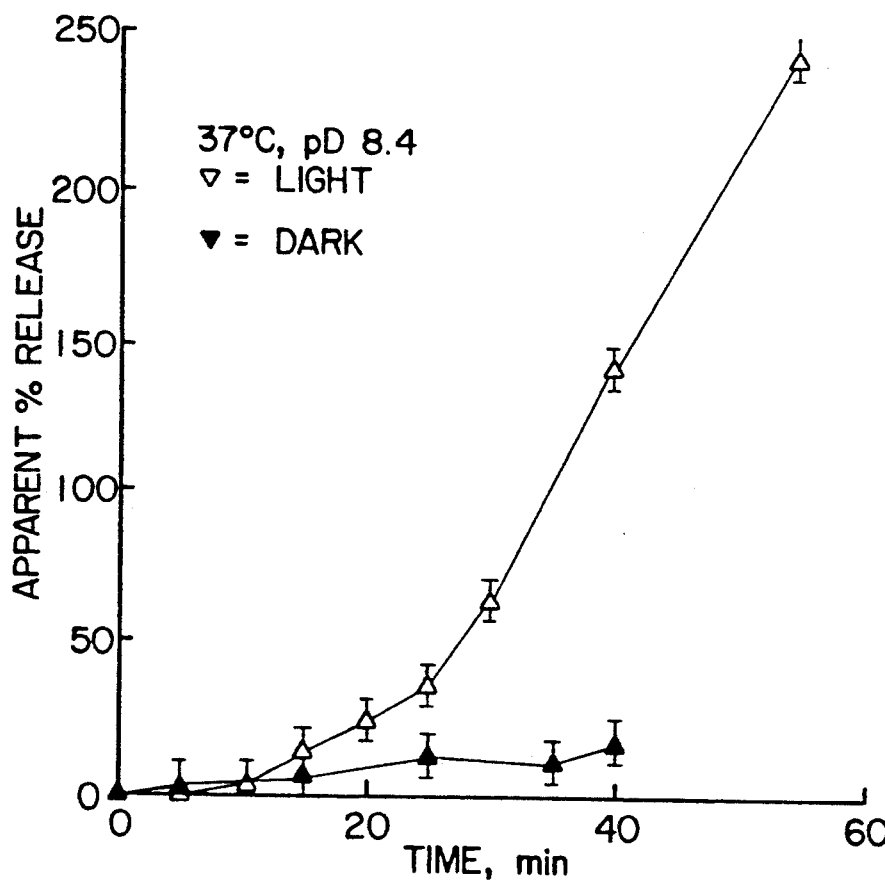
FIG. 11 is a graph similar to FIG. 10 showing apparent glucose release from PlasPPC/DHC (30 mol %) liposomes in 20 mM Tris/D$_2$O/100 mM NaCl, pD 8.4, 37° C. after 630 nm irradiation (△); and in the dark (▲).

Photoinduced contents leakage was also measured in vesicles prepared with Tris/D$_2$O/NaCl buffer (FIG. 11). Following a short induction period (ca. 10 min), the apparent release rate increases dramatically to a final value of more than 200% after 55 minutes of irradiation. This result is consistent with liposome aggregation or fusion.

Figure 12:
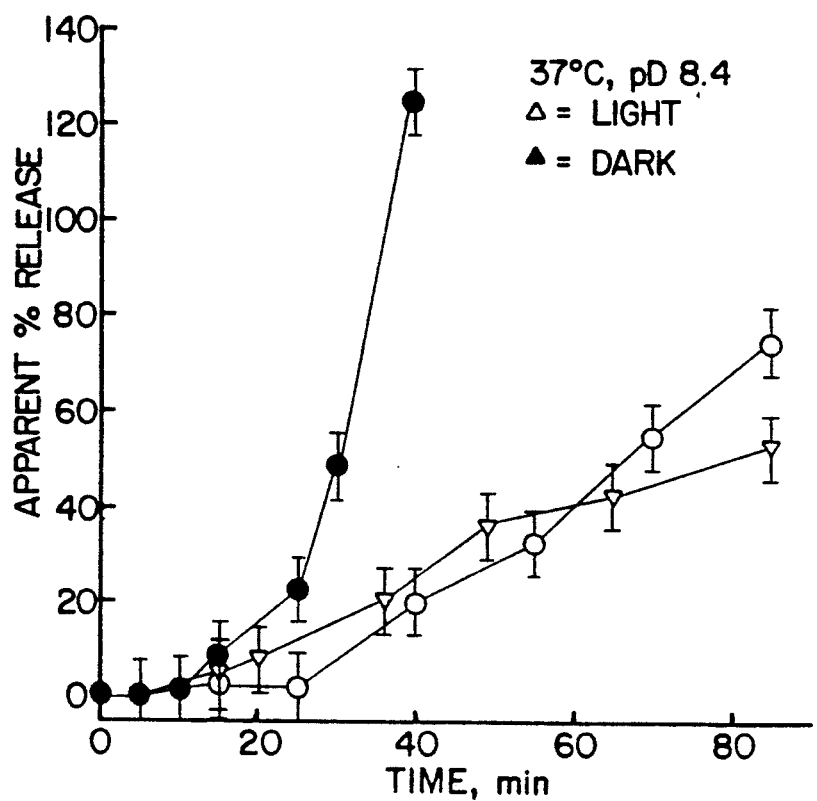
FIG. 12 is a graph showing apparent glucose release kinetics from irradiated (λ>630 nm) PlasPPC/DHC liposomes at 37° C. (▽) in 20 mM Tris/H$_2$O/100 mM NaCl at pH 8; (●) 20 mM Tris/100 mM NaN$_3$ at pH 8; (○) 20 mM Tris/D$_2$O/100 mM NaCl at pD 8.4.

The purely light-induced changes in liposome contents leakage were illustrated in FIG. 12 by subtracting dark permeation rates from those of irradiated liposomes (FIGS. 9, 10, 11) and replotted in FIG. 12. In all cases (i.e., Tris/NaCl, Tris/NaN$_3$, Tris/D$_2$O/NaCl), a distinct induction period is observed, ranging from 10 to 30 minutes. Similar studies of glucose leakage accompanying sensitization by membrane-bound phthalocyanine showed no such lag-time.

TLC analysis of liposomes after irradiation indicated the formation of several new products each more polar than starting PlasPPC. Table III gives the R$_f$s in 65:35:6 CHCl$_3$/MeOH/NH$_4$OH of products from photolysis (90 minutes) of PlasPPC/DHC/Tris/NaCl liposomes as well as those from Tris/azide and Tris/D$_2$O/NaCl experiments. Authentic samples of D-glucose, DHC, PlasPPC and 1-palmitoyl-sn-glycero-3-phosphocholine (LysoPC) were also spotted. In each case, an aliquot from the associated dark control sample was also spotted. All dark samples showed only a single spot with R$_f$ 0.54 corresponding to that of PlasPPC.

TABLE III

| TLC of Photolysis of PlasPPC/DHC/AlClPcS Liposomes | | | | |
|---|---|---|---|---|
| Compound | R$_f$ | | | |
| PlasPPC | 0.54 | | | |
| DHC | 1.0 | | | |
| Glucose | 0.09 | | | |
| LysoPC | 0.27 | | | |
| PlasPPC/DHC Liposomes: | | | | |
| Tris/NaCl | 0.23, | 0.55 | | |
| Tris/NaN$_3$ | 0.26, | 0.55 | | |
| Tris-D$_2$O/NaCl | 0.16, | 0.22, | 0.32, | 0.50 |

Photoinduced morphology changes of liposomes in Tris/$D_2O$/NaCl were evidenced by a large increase in solution turbidity. As particle size increases, the solution turbidity increases.

This Example illustrates the potential of a water-soluble phthalocyanine, such as AlClPcS, to produce ROS which stimulate release of entrapped glucose from a plasmalogen liposome. This study differs from Example I in that the sensitizer in Example II is localized in the hydrophilic core of the liposome, away from the vinyl ether linkage. Lipid peroxidation requires diffusion of the ROS across the bilayer/aqueous interface. Although quantitative measures vary substantially, the penetration efficiency of $^1O_2$ through the phosphatidylcholine/water bilayer interface seems to be less than that observed in either isotropic solution or in micelles. Secondly, DSC data indicates that in contrast to PlasPPC/DPPC liposomes, PlasPPC/DHC vesicles are in the gel phase at 37° C., in which oxygen has reduced solubility. Finally, DHC stabilizes the bilayer structure and reduces thermal permeation of glucose. Addition of steroids like cholesterol and DHC increases viscosity of bilayer membranes. Hence, diffusion of ROS to the vinyl ether linkage may be slower in PlasPPC/DHC liposomes than the PlasPPC/DPPC vesicles of Example I.

Figure 13:
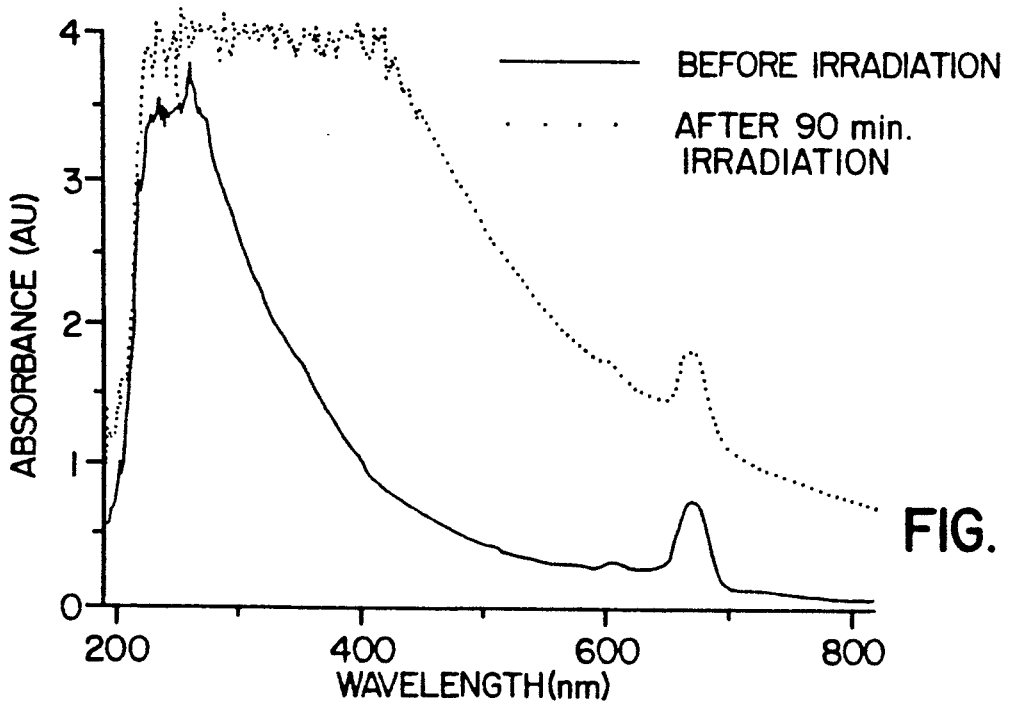
FIG. 13 is an absorption spectrum of PlasPPC/DHC (30 mol %) liposomes in 20 mM Tris/D$_2$O/100 mM NaCl before (—) and after (····) 90 minutes of photolysis (λ>630 nm).
Figure 14:
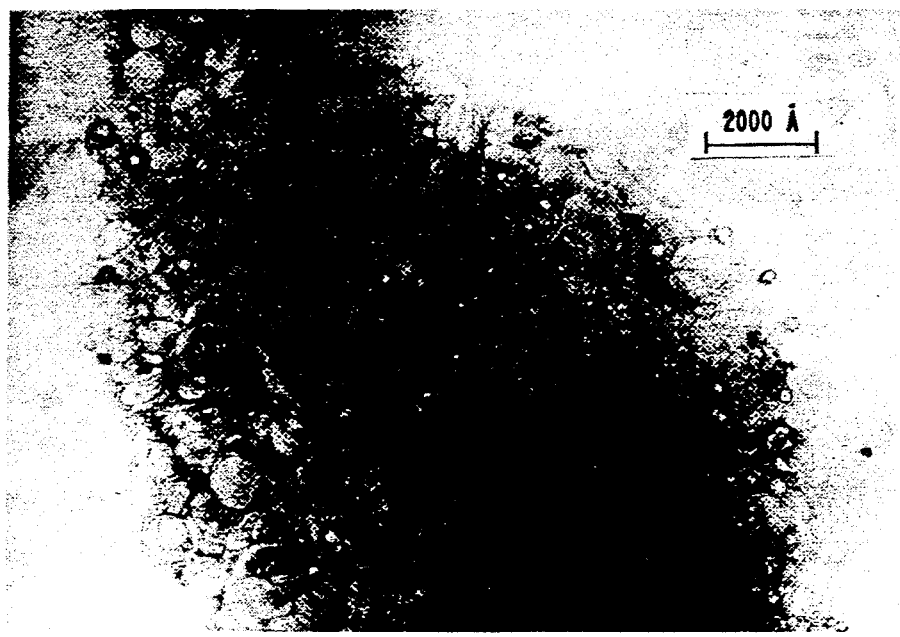
FIGS. 14 and 15 are photomicrographs showing negative stain (2% ammonium molybdate, pH 8 Tris) transmission electron micrographs of PlasPPC/DHC (30 mol %) liposomes before (FIG. 14) and after (FIG. 15) 100 minutes of sensitized photolysis (λ>630 nm).
Figure 15:
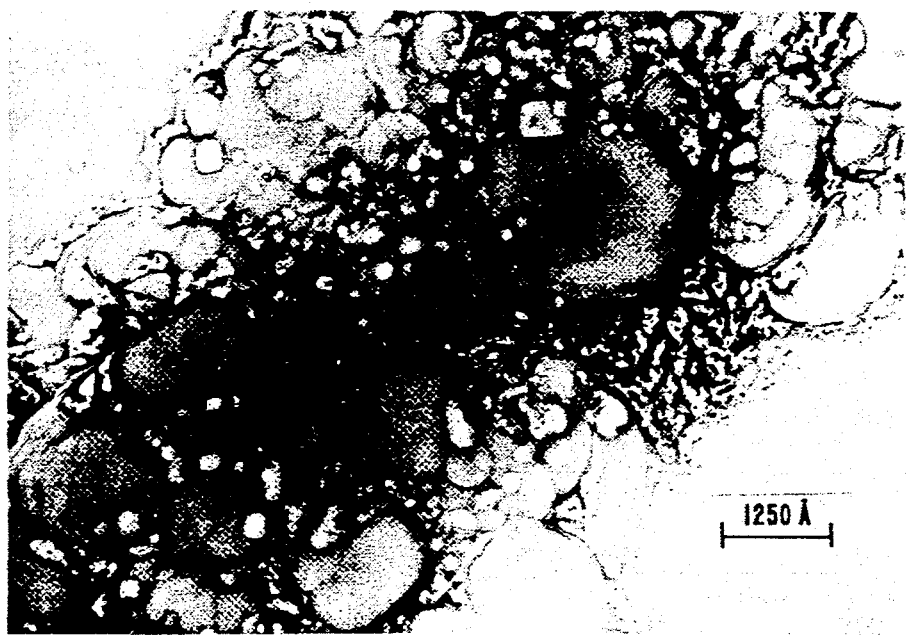

The data in FIG. 12 clearly demonstrate that PlasPPC/DHC liposomes are affected by irradiation in the presence of oxygen. The observation of a glucose release greater than 100% suggests that some photoinduced morphological changes have caused an increase in light scattering of the liposomes independent of any increases due to reduction of NADP. Changes in liposome size and structure are confirmed by electron microscopy (FIGS. 14 and 15) which shows a substantial increase in the average liposome size after visible irradiation (FIG. 15). The abundance of large diameter (>1200 A) multilamellar structures in the micrographs of the photolyzed sample (FIG. 15) is most likely responsible for the increased tailing observed throughout the absorption spectrum (FIG. 13). Finally, the abundance of large, multilamellar structures in the micrographs suggests that a significant portion of glucose was released by photolysis.

Electron micrographs of PlasPPC/DHC liposomes in 20 mM Tris/$D_2O$/NaCl before and after irradiation (FIGS. 14 and 15, respectively) indicate a much larger population of large, multilamellar vesicles following photolysis. Before photolysis, the liposomes (extruded through stacked 0.05 μm Nucleopore filters for this experiment) were unilamellar and exhibit a narrow size distribution with median diameter of 600 A. In contrast, irradiated vesicles were predominantly multilamellar and statistically much larger, with a median diameter of 1100–1200 A.

TLC results indicate the formation of new products in the photolyzed samples not found in the dark controls. The observation that the major product formed during photolysis exhibits an $R_f$ very similar to that of LysoPC suggests that the predominant reaction induced by AlClPcS sensitization is cleavage of a lipid chain. The saturated nature of the sn-2 chain in PlasPPC makes it more likely that such a reaction would take place at the vinyl ether linkage of the sn-1 chain.

The absorbance of spectra of liposomes before and after photolysis are given in FIG. 13, and show that a large increase in liposomal scattering has resulted from irradiation. Such an effect could be induced by aggregation and/or fusion of the liposomes. No comparable change in the scattering properties was observed in the absorption spectrum of liposomes used in the dark control.

This Example shows that PlasPPC forms unilamellar vesicles when combined with DHC at concentrations of 30 mol %. Passive permeation at 37° C. of encapsulated glucose is less than that observed in PlasPPC/DPPC vesicles that contain lysolipid contaminants. Visible irradiation of PlasPPC/DHC liposomes in the presence of AlClPcS entrapped within the aqueous core results in significant changes in size and morphology of the vesicles as well as formation of new photoproducts. Observation of an induction time in apparent glucose release plots is consistent with an ROS-dependent mechanism for photoinduced morphology changes.

EXAMPLE III

Figure 16:
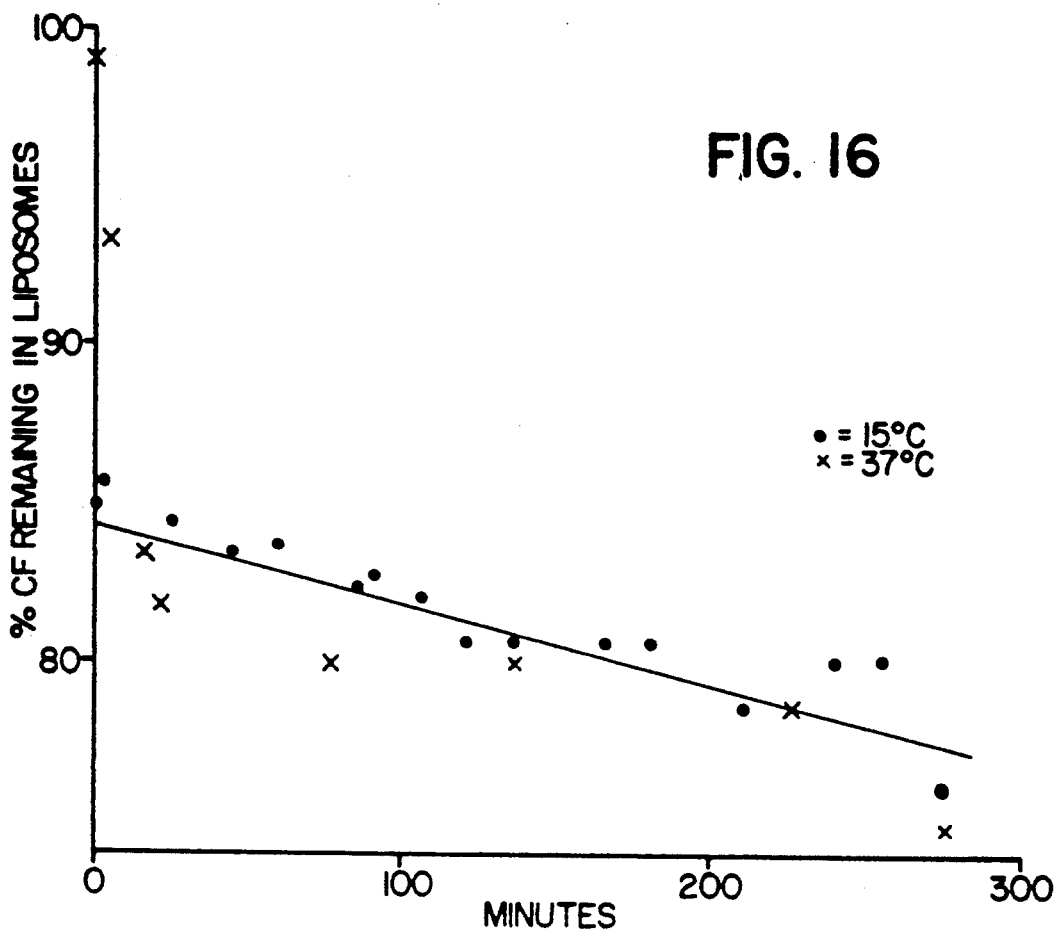
FIG. 16 is a plot showing percent of carboxy fluorescein remaining as a function of time during passive release of the fluorescent marker from pure plasmalogen liposomes.

Pure dialkyl plasmalogen liposomes were prepared as in Examples I or II by first purifying the plasmalogen starting material by chromatography, and not adding a DHC or DPPC colipid stabilizer. The plasmalogen was purified such that it was substantially completely in the dialkyl form, that is it contained less than 20% lysolipid, and preferably less than 2% lysolipid. It was loaded with a drug or other substance as already described. FIG. 16 shows passive release of a fluorescent marker (carboxyfluorescein) from the pure non-illuminated plasmalogen liposomes. This demonstrates that leakage properties of pure PlasPPC liposomes does not differ substantially from the PlasPPC/DPPC (8.5:1) data.

EXAMPLE IV

Other examples of plasmalogens that would be suitable for making the liposomes of the present invention include bis-vinyl ether lipid (having an sn-1 and sn-2 chain) or (sn-1)$_2$ or (sn-2)$_2$; mono or bis-enamine; mono or bis-vinyl ether that is non-glycerol based.

EXAMPLE V

Figure 17:
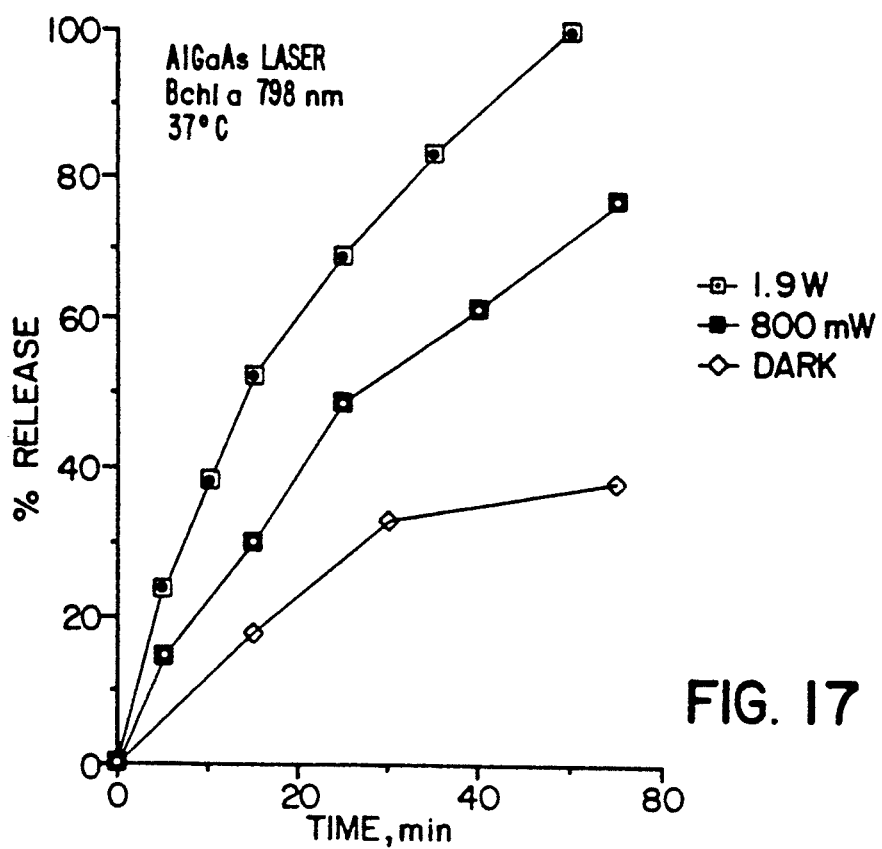
FIG. 17 is a graph showing liposome release after illumination with a laser at varying powers.

The dose or characteristics of the illumination source are not known to have any critical parameters, although preferred characteristics of the illumination source have been described in earlier Examples. The illumination has, however, been found to produce a dose related liposome response that is demonstrated in this Example. The liposomes were prepared as in Example I above, but the ZnPc sensitizer was replaced with bacteriochlorophyll a as a sensitizer. The illumination source was a 3 watt aluminum/gallium/arsenic laser with a laser output at 798 nm. The intensity (in the solution) was adjusted to give 600 milliwatts or 1.9 watts of power. Data are shown in FIG. 17 for glucose release at 37° C. Glucose release was shown to increase as the laser power increased.

EXAMPLE VI

In clinical use, the plasmalogen liposomes of the present invention would be administered intravenously. The patient would receive IV liposomes containing, for example, cytotoxic cancer chemotherapeutic drugs, as in U.S. Pat. No. 3,993,754 which is incorporated by reference, or as in administration of doxorubicin in Forssen, Proc. Natl. Acad. Sci. USA 78:1873–1877 (1981) and Forssen, Cancer Res. 43:546–550 (1983) which are also incorporated by reference. The target area, such as a neoplasm (for example, adenocarcinoma of the lung or large intestine) would be irradiated within an hour of the injection with any of the illumination sources described in the Examples above. It would be desirable to prepare the liposomes immediately before administration if the liposome is not stabilized for a sustained shelf life. In clinical practice, a preferred light source would be an endoscope having a diffuser tip attached to the fiberoptic bundle. A laser, such as the aluminum/gallium/arsenic laser of Example V, could preferably be used to illuminate a target, particularly a small tumor or micrometastasis. Other suitable illumination sources include filtered tungsten, xenon or mercury light sources, and pump lasers.

It is also possible to select a photodynamic sensitizer that has a cytotoxic effect, and use it to cleave the vinyl ether functionality. Such a liposomal system would have the advantage of delivering the sensitizer to a target site.

EXAMPLE VII

The liposomes of the present invention can also be used to deliver cosmetics to a target site. A moisturizer would be incorporated into the liposome, and applied topically to a desired target site. A sensitizer could be chosen that has a λ max that corresponds to ambient room light. The liposomal contents would then be released at the target site by photolysis mediated by room light.

Having illustrated and described the principles of the invention in many preferred embodiments, it should be apparent to those skilled in the art that the invention can be modified in arrangement and detail without departing from such principles. We claim all modifications coming within the spirit and scope of the following claims.

We claim:

1. A liposome comprising:
   a liposomal membrane consisting essentially of plasmalogens having a phospholipid with a vinyl ether functional group sufficiently close to an interface between the membrane and its environment or core that, when the vinyl ether functional group is cleaved to produce a product that forms a micelle in the membrane, pores are formed in the membrane through which the contents of the liposome may leave the liposome; and
   a lysogenic substance that, in response to photoillumination or pH reduction, produces reactive oxygen species or hydrogen ions which cleave the vinyl ether functional group of the plasmalogen in response to photoillumination or pH reduction and form the pores in the membrane.

2. The liposome of claim 1 wherein the lysogenic substance produces reactive oxygen species that cleave the vinyl ether functional group in response to photoillumination or pH reduction.

3. The liposome of claim 1 wherein the lysogenic substance absorbs light and produces reactive oxygen species, in response to illumination of the lysogenic substance with light, which reactive oxygen species cleave the vinyl ether functional group.

4. The liposome of claim 1 wherein the lysogenic substance produces reactive oxygen species in response to illumination of the lysogenic substance with light having a wavelength greater than about 630 nm.

5. The liposome of claim 1 wherein the lysogenic substance produces hydrogen ions in response to photoillumination to lower the pH and cleave the vinyl ether functional group.

6. The liposome of claim 5 wherein the lysogenic substance produces hydrogen ions in response to photoillumination of the lysogenic substance with light of a wavelength that is absorbed by the lysogenic substance.

7. The liposome of claim 6 wherein the lysogenic substance produces hydrogen ions in response to photoillumination with light having a wavelength of 540-827 nm.

8. The liposome of claim 1 wherein the phospholipid comprises the compound:

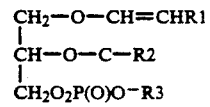

wherein $R_1$ and $R_2$ each comprise $(CH_2)_n$ where n is 12-24 and $R_3$ is selected from the group consisting of choline, ethanolamine, serine and inositol.

9. The liposome of claim 8 wherein n is 12-16.

10. The liposome of claim 8 wherein n is 16-18.

11. The liposome of claim 8 wherein n is 12-16 for $R_1$ and n is 16-24 for $R_2$.

12. The liposome of claim 1 wherein the phospholipid comprises a polar head group and two lipophilic chains, wherein only one of the lipophilic chains contains the vinyl ether functionality.

13. The liposome of claim 1 further comprising a therapeutic substance contained within the cavity or membrane of the liposome.

14. The liposome of claim 13 wherein the therapeutic substance is contained in the lipid bilayer.

15. The liposome of claim 13 wherein the therapeutic substance is contained in the cavity.

16. The liposome of claim 14 wherein the lysogenic substance is contained in the cavity.

17. The liposome of claim 15 wherein the lysogenic substance is contained in the membrane.

18. The liposome of claim 1 wherein the liposomal membrane also comprises a stabilizing lipid, selected from the group consisting of dihydrocholesterol and dipalmitoyl phosphatidylcholine, in an amount sufficient to enhance liposome stabilization.

19. The liposome of claim 1 wherein the lysogenic substance is a phthalocyanine.

20. A liposome, comprising:
    a liposomal membrane consisting essentially of a plasmalogen lipid that contains a vinyl ether functional group which, when cleaved, produces a micelle that forms a stable pore in the membrane;
    a lysogenic substance that locally reduces the pH or produces reactive oxygen species in response to illumination with light absorbed by the substance to cleave the vinyl ether functionality; and
    a therapeutic substance carried by the liposome and released from the liposome through the pore in the membrane after illumination.

21. The liposome of claim 20 wherein the liposomal membrane encloses a cavity in which the therapeutic substance is contained, and the lysogenic substance is contained in the membrane.

22. The liposome of claim 20 wherein the liposomal membrane encloses a cavity, and the therapeutic substance is contained within the membrane and not the cavity.

23. The liposome of claim 1 wherein the membrane consists of plasmalogens having the vinyl ether functional group within 9 carbons of the interface.

24. The liposome of claim 1 wherein the membrane consists of plasmalogens having the vinyl ether functional group within 4 carbons of the interface.

25. The liposome of claim 24 wherein the membrane consists of plasmalogens in which the vinyl ether functional group is at the interface with no intervening carbons between the interface and functionality.

26. The liposome of claim 1 wherein the sensitizer is selected from the group consisting of a phenathiazinequinone, bis(2-ethyl-1,3'-dioxolane)kryptocyanine, purpurin, phthalocyanine, and a clorin.

27. The liposome of claim 26 wherein the sensitizer is a phthalocyanine selected from the group consisting of 2,6,16,23-tetrahydroxy phthalocyanines, sulfonated naphthalocyanines, and octaalkoxy phthalocyanines.

* * * * *

UNITED STATES PATENT AND TRADEMARK OFFICE
CERTIFICATE OF CORRECTION

PATENT NO.  : 5,277,913
DATED       : January 11, 1994
INVENTOR(S) : David H. Thompson et al.

It is certified that error appears in the above-indentified patent and that said Letters Patent is hereby corrected as shown below:

Column 4, line 52, "(●) 20 mM" should read --(○) 20 mM--.

Column 4, line 53, "(○) 20 mM" should read --(●) 20 mM--.

Column 12, line 48, "(50 ‖1" should read --50 µ1--.

Column 22, line 8, "540" should read --640--.

Signed and Sealed this

Third Day of October, 1995

Attest:

BRUCE LEHMAN

Attesting Officer    Commissioner of Patents and Trademarks